US012692308B2

(12) United States Patent
Antignano

(10) Patent No.: US 12,692,308 B2
(45) Date of Patent: Jul. 28, 2026

(54) KITS, COMPOSITIONS AND METHODS FOR CELL ENRICHMENT

(71) Applicant: STEMCELL Technologies Canada Inc., Vancouver (CA)

(72) Inventor: Frann Antignano, Vancouver (CA)

(73) Assignee: STEMCELL Technologies Canada Inc., Vancouver (CA)

( * ) Notice: Subject to any disclaimer, the term of this patent is extended or adjusted under 35 U.S.C. 154(b) by 1065 days.

(21) Appl. No.: 15/734,791

(22) PCT Filed: Jun. 6, 2019

(86) PCT No.: PCT/CA2019/050787
§ 371 (c)(1),
(2) Date: Dec. 3, 2020

(87) PCT Pub. No.: WO2019/232631
PCT Pub. Date: Dec. 12, 2019

(65) Prior Publication Data
US 2021/0230542 A1 Jul. 29, 2021

Related U.S. Application Data

(60) Provisional application No. 62/681,224, filed on Jun. 6, 2018.

(51) Int. Cl.
| | |
|---|---|
| *C07K 16/28* | (2006.01) |
| *C12N 5/078* | (2010.01) |
| *C12N 5/0786* | (2010.01) |

(52) U.S. Cl.
CPC ............ *C07K 16/28* (2013.01); *C12N 5/0634* (2013.01); *C12N 5/0645* (2013.01)

(58) Field of Classification Search
None
See application file for complete search history.

(56) References Cited

U.S. PATENT DOCUMENTS

| | | | |
|---|---|---|---|
| 2002/0081635 A1 | 6/2002 | Thomas et al. | |
| 2014/0302483 A1 | 10/2014 | Kauling et al. | |
| 2015/0204765 A1* | 7/2015 | Kokaji | G01N 33/543 |
| | | | 435/7.25 |
| 2015/0301045 A1* | 10/2015 | Chronopoulou | G01N 33/56972 |
| | | | 506/18 |
| 2018/0057795 A1 | 3/2018 | Childs et al. | |

FOREIGN PATENT DOCUMENTS

| | | |
|---|---|---|
| CA | 2178984 A1 | 12/1996 |
| CN | 1367876 A | 9/2002 |
| CN | 103260650 A | 8/2013 |
| EP | 1621550 A1 | 2/2006 |
| WO | 2016/197238 A1 | 12/2016 |
| WO | 2017017184 A1 | 2/2017 |

OTHER PUBLICATIONS

Movahedi et al., Blood (2008) 111 (8): 4233-4244, Identification of discrete tumor-induced myeloid-derived suppressor cell subpopulations with distinct T cell-suppressive activity. (Year: 2008).*
Extended Search Report as received in connection to EP Application No. 19815351.2, mailed on Feb. 16, 2022, pp. 1-12.
"Mouse Neutrophil Enrichment Kit", Internet Citation, Stemcell Jul. 2010, pp. 1-2.
"Neutrophil isolation kit mouse", Biotec Miltenyi, Feb. 9, 2016, pp. 1-3.
Hasenberg, M. et al., Rapid Immunomagnetic Negative Enrichment of Neutrophil Granulocytes from Murine Bone Marrow for Functional Studies In Vitro and In Vivo, Plos One, Public Library of Science US, vol. 6, No. 2, e17314, Jan. 1, 2011, pp. 1-11.
Veglia, Filippo et al, "Myeloid-derived suppressor cells coming of age", Nature Immulogy, Nature Publishing Group, US. New York, vol. 19, No. 2., 2018, pp. 108-119.
Peters, C.E., et al., "Isolation of Subsets of Immune Cells", Methods in Molecular Biology, 2005, vol. 302, pp. 95-115, ISSN 1064-3745.
Coquery, C.M., et al., "Optimized protocol for the isolation of spleen-resident murine neutrophis", 2012, Cytometry A, vol. 81A, pp. 801-814, ISSN 1552-4922.
Bronte, V., et al., "Recommendations for myeloid-derived suppressor cell nomenclature and characterization standards", Jul. 6, 2016, Nat. Commun., vol. 7, Article 12150, DOI: 10.1038/ncomms12150, ISSN 2041-1723.
CD Marker Handbook, 2010, bdbiosciences.com/go/humancdmarkers, pp. 1-47.
Movahedi, K. et al., "Identification of discrete tumor-induced myeloid-derived suppresor cell subpopulations with distinct T cell-suppressive activity", Blood, Apr. 15, 2008, vol. 111, No. 8, pp. 4233-4244. https://doi.org/10.1182/blood-2007-07-099226.

* cited by examiner

*Primary Examiner* — Daniel E Kolker
*Assistant Examiner* — Cheom-Gil Cheong
(74) *Attorney, Agent, or Firm* — SMART & BIGGAR LP

(57) ABSTRACT

Kits, compositions and methods for enriching myeloid-derived suppressor cells (MDSCs) are provided. In one embodiment, the kit comprises (a) one or more antibodies or fragments thereof that bind one or more non-MDSC target cells; and (b) a plurality of particles, wherein the plurality of particles are linked or linkable to at least one of the one or more antibodies.

20 Claims, 13 Drawing Sheets

A

B

C

D

E

F

A

Cocktail Version 1

CD8
B220 (CD45R)
Ter119
CD49b
CD19
CD11c
TCRg/d
CD24
TCRa/b
CD4

B

| Start | Direct Isolation | Indirect Isolation |
|:---:|:---:|:---:|

A

Cocktail Version 2

CD8
B220 (CD45R)
Ter119
CD49b
CD19
CD11c
TCRg/d
CD24
TCRa/b
CD4
CD5

A

Cocktail Version 3

CD8
B220 (CD45R)
Ter119
CD49b
CD19
CD11c
TCRg/d
CD24
TCRa/b
CD4
CD5
F480

B

Start

Direct Isolation

A

Cocktail Version 4

| |
| --- |
| CD8 |
| B220 (CD45R) |
| Ter119 |
| CD49b |
| CD19 |
| CD11c |
| TCRg/d |
| CD24 |
| TCRa/b |
| CD4 |
| CD5 |
| F480 |
| CD2 |
| cKit |

B

Start                              Direct Isolation

A

Cocktail Version 5

| CD8 |
|---|
| B220 (CD45R) |
| Ter119 |
| CD49b |
| CD19 |
| CD11c |
| TCRg/d |
| CD24 |
| TCRa/b |
| CD4 |
| CD5 |
| CD2 |
| cKit |

B

Start                                    Direct Isolation

A

Cocktail Version 6

CD8
B220 (CD45R)
Ter119
CD49b
CD19
CD11c
TCRg/d
CD24
TCRa/b
CD4
CD5
CD2
cKit
CD31

B

Start

Direct Isolation

Indirect Isolation

A

Cocktail Version 7

CD8
Ter119
CD49b
CD19
CD11c
TCRg/d
CD24
TCRa/b
CD4
CD5
CD2
cKit
CD31

B

Start

Direct Isolation

A

Cocktail Version 8

| |
|---|
| CD8 |
| B220 (CD45R) |
| Ter119 |
| CD49b |
| CD19 |
| CD11c |
| TCRg/d |
| TCRa/b |
| CD4 |
| CD5 |
| CD2 |
| cKit |
| CD31 |

B

Start

Direct Isolation

A

CD4+ cell proliferation

CD8+ cell proliferation

▨ Unstimulated splenocytes

━ Stimulated splenocytes

━ MDSC 1:1

⋯ MDSC 1:4

⋯ MDSC 1:16

B

KITS, COMPOSITIONS AND METHODS FOR CELL ENRICHMENT

CROSS-REFERENCE TO RELATED APPLICATION

This application is a national Phase entry application of Patent Cooperation Treaty Application No. PCT/CA2019/050787, filed Jun. 6, 2019, which claims the benefit of priority to U.S. Provisional Application No. 62/681,224 filed Jun. 6, 2018, the contents of which are incorporated herein by reference in their entirety.

FIELD

The present disclosure relates to kits, compositions, and methods for enriching cells of interest. More particularly, the disclosure relates to kits, compositions and methods for enriching myeloid-derived suppressor cells (MDSCs).

BACKGROUND

The hematopoietic system is responsible for the generation of all the cells found in the blood including red blood cells, platelets and the leukocytes that make up the immune system. Among the functions of cells of the immune system, certain of these cells defend against attack from pathogens and other insults. In addition, the cells of the immune system are important for surveilling host tissues for cells that have become cancerous. When immune cells fail to function optimally, conditions such as autoimmune diseases and cancer progression can result.

The cells of the immune system are very complex and can be broadly divided into innate and adaptive cell types. Within these branches are multiple subtypes of cells, each with their own unique functions, as well as complex interactions between different cell types. Researchers are increasingly interested in studying and analyzing the properties and function(s) of a given cell type of the immune system.

Myeloid-derived suppressor cells (MDSCs) are of particular interest to researchers in both the fields of inflammation and cancer. MDSCs are a population of blood cells that regulate immune responses in cancer, chronic infections and inflammatory conditions, and organ transplant. MDSCs are understood to be absent in healthy individuals, but are induced in response to soluble factors secreted by most tumours. In a subject with a tumour burden, bone marrow (BM)-derived MDSCs accumulate in peripheral lymphoid organs and the tumour microenvironment. BM-derived MDSCs may also be detected in circulation and at pre-metastatic sites. In several human cancers, and in experimental tumour models in animals, the presence of high numbers of MDSCs correlates with tumour growth and metastasis, and overall poor prognosis. Therapeutic approaches that block MDSC activity or deplete MDSC populations have shown promising efficacy in the treatment of cancer in animal models. Thus, MDSC biology is a highly active field in biomedical research.

Cell separation methods that effectively and efficiently separate cells of interest from other cell types present in a sample are extremely important tools for immune cell researchers. A current approach to isolate MDSCs requires sorting cell subsets by multi-colour flow cytometry. Alternatively, Miltenyi Biotec Inc. (MBI) manufactures a mouse MDSC isolation kit based on a two-step positive immunomagnetic separation approach to enrich for cells expressing cell-surface markers typical of MDSC cell populations, such as $Gr1^{hgh}Ly6G^{high}$ and $Gr1^{low}Ly6G^{neg}$ cell populations. In the first step, the sample cell population is enriched for $Ly6G^{high}$ cells by positive selection using a Ly6G-specific antibody (Ab). The flow-through from this first step contains $Gr1^{low}Ly6G^{neg}$ cells that are enriched in the second step using a Gr1-specific Ab and positive immunomagnetic selection. The MBI mouse MDSC isolation kit has several shortcomings that limit its utility for MDSC biology research. This procedure is not only time consuming but the use of positive selection results in isolated cells that are coated with antibodies and magnetic particles, which may have unintended consequences. For example, positively selected MDSCs may become activated thereby interfering with their function. Further, if positively-selected cells are intended to be (re-) introduced into a recipient, they may become depleted by the recipient's immune system; Gr1, in particular, is known to be a depleting antibody in vivo.

New kits, compositions, and methods are desired to enrich for MDSCs.

SUMMARY

The present disclosure provides kits, compositions and methods for enriching myeloid-derived suppressor cells (MDSCs) from a sample comprising target cells and MDSCs using one or more antibodies or fragments thereof that bind one or more target cells. One advantage of the kits, compositions and methods of the disclosure is the enrichment of MDSCs using a single, negative selection step. A further advantage of the kits, compositions and methods of the disclosure is the enrichment of MDSCs at a high level of purity (i.e. are pure or substantially pure) and at a high level of recovery. A still further advantage of the kits, compositions and methods of the disclosure is that the enriched MSDCs are not associated with, or coupled to, any antibodies or particles used during the enrichment process.

Accordingly, in one aspect of this disclosure, kits are provided for enriching myeloid-derived suppressor cells (MDSCs) from a sample comprising target cells and MDSCs, the kits comprising:

one or more antibodies or fragments thereof that bind one or more target cells; and a plurality of particles, wherein the plurality of particles are linked or linkable to at least one of the one or more antibodies.

In one embodiment, the target cells comprise one or more of B cells, T cells, NK cells, dendritic cells, monocytes/macrophages, basophils, mast cells, platelets, endothelial cells, granulocytes or red blood cells, or any subtype or progenitor thereof.

In another embodiment, the one or more antibodies or fragments thereof bind one or more antigens or epitopes thereof on the target cells, wherein:

i) the B cell antigens are selected from one or more of B220, CD19, CD2, CD5, and CD31;

ii) the T cell antigens are selected from one or more of CD8, TCRg/d, TCR a/b, CD4, CD5, CD2, and CD31;

iii) the NKcell antigens are selected from one ormore of CD49b and CD2;

iv) the dendritic cell antigens are selected from one or more of CD11c and CD31;

v) the monocyte/macrophage antigen is selected from one or more of CD2 and CD31;

vi) the basophils antigen is CD49b;

vii) the mast cell antigen is cKit;

viii) the platelet antigen is CD31;

ix) the endothelial cell antigen is CD31;

x) the granulocyte antigen is CD31; and xi) the red blood cell antigens are selected from one or more of Ter119 and CD24.

In one embodiment, the target cells comprise, consist of, or consist essentially of:

(a) T cells, B cells, red blood cells, granulocytes, dendritic cells, and NKcells, (b) T cells, B cells, red blood cells, granulocytes, dendritic cells, NK cells and macrophages, (c) T cells, B cells, red blood cells, granulocytes, dendritic cells, NK cells, macrophages, mast cells and hematopoieticprogenitors, (d) T cells, B cells, red blood cells, granulocytes, dendritic cells, NK cells, mast cells and hematopoietic progenitors, or (e) T cells, B cells, red blood cells, dendritic cells, NK cells, macrophages, mast cells, hematopoietic progenitors, monocytes, granulocytes and endothelial cells.

In another embodiment, the one or more antibodies comprise a first linkage moiety. Optionally, the first linkage moiety is biotin, or any modification, derivative, or analogue thereof.

In another embodiment, the plurality of particles comprise a second linkage moiety directly or indirectly linked or linkable to the first linkage moiety. Optionally, the second linkage moiety is streptavidin, or any modification, derivative, or analogue thereof.

In another embodiment, the kit further comprises a tetrameric antigen complex (TAC), wherein the TAC comprises a first antibody that binds to the first linkage moiety and a second antibody that binds to the second linkage moiety and the first antibody and the second antibody are indirectly linked.

In another embodiment, the plurality of particles have a density within a density range of the target cells.

In another embodiment, the plurality of particles have a density outside a density range of the target cells.

In another embodiment, the plurality of particles are less dense than the density range of the target cells and are buoyant when linked to the target cells.

In another embodiment, the plurality of particles are more dense than the target cells.

In another embodiment, the plurality of particles are magnetic or magnetizable.

In another aspect of this disclosure are provided compositions for enriching myeloid-derived suppressor cells (MDSCs) from a sample comprising target cells and MDSCs, comprising: at least two, at least 3, at least 4, at least 5, at least 6, at least 7 or at least 8 antibodies or fragments thereof, wherein each antibody or fragment thereof binds a different antigen or epitope thereof of one or more target cells selected from the group consisting of: B cells, T cells, NK cells, dendritic cells, monocytes/macrophages, basophils, mast cells, platelets, endothelial cells, granulocytes or red blood cells and any subtype or progenitor thereof.

In one embodiment, the composition comprises, consists of, or consists essentially of antibodies or fragments thereof that bind:

(a) T cells, B cells, red blood cells, granulocytes, dendritic cells, and NKcells, (b) T cells, B cells, red blood cells, granulocytes, dendritic cells, NK cells and macrophages, (c) T cells, B cells, red blood cells, granulocytes, dendritic cells, NK cells, macrophages, mast cells and hematopoieticprogenitors, (d) T cells, B cells, red blood cells, granulocytes, dendritic cells, NK cells, mast cells and hematopoietic progenitors, or (e) T cells, B cells, red blood cells, dendritic cells, NK cells, macrophages, mast cells, hematopoietic progenitors, monocytes, granulocytes and endothelial cells.

In another aspect of this disclosure are provided methods for enriching myeloid-derived suppressor cells (MDSCs) from a sample comprising target cells and MDSCs, comprising:

contacting the sample with one or more antibodies or fragments thereof that bind one or more target cells, and a plurality of particles, wherein the plurality of particles are linked or linkable to at least one of the antibodies;

incubating the target cells, antibodies, and particles to form target cell:particle complexes; and separating the target cell:particle complexes from the sample to enrichthe MDSCs.

In one embodiment, the target cells are one or more of B cells, T cells, NK cells, dendritic cells, monocytes/macrophages, basophils, mast cells, platelets, endothelial cells, granulocytes or red blood cells, or any subset or progenitor thereof.

In another embodiment, the one or more antibodies or fragments thereof bind one or more antigens or epitopes thereof on the target cells, and wherein:

i) the B cell antigens are selected from one or more of B220, CD19, CD2, CD5, and CD31;

ii) the T cell antigens are selected from one or more of CD8, TCRg/d, TCR a/b, CD4, CD5, CD2, and CD31;

iii) the NK cell antigens are selected from one or more of CD49b and CD2;

iv) the dendritic cell antigens are selected from one or more of CD11c and CD31;

v) the monocyte/macrophage antigen is selected from one or more of CD2 and CD31;

vi) the basophils antigen is CD49b;

vii) the mast cell antigen is cKit;

viii) the platelet antigen is CD31;

ix) the endothelial cell antigen is CD31;

x) the granulocyte antigen is CD31; and xi) the red blood cell antigens are selected from one or more of Ter119 and CD24.

In another embodiment, the one or more antibodies comprise a first linkage moiety. Optionally, the first linkage moiety is biotin, or any modification, derivative, or analogue thereof.

In another embodiment, the plurality of particles comprise a second linkage moiety directly or indirectly linked or linkable to the first linkage moiety. Optionally, the second linkage moiety is streptavidin, or any modification, derivative, or analogue thereof.

In another embodiment, the method further comprises pre-linking the antibodies and particles before contacting the sample.

In another embodiment, the separation is by sedimentation.

In another embodiment, the separation is by density separation.

In another embodiment, the plurality of particles are buoyant.

In another embodiment, the plurality of particles are magnetic or magnetizable.

In another embodiment, the method further comprises exposing the target cell:particle complexes to a magnetic field.

In another embodiment, the sample is a cell suspension.

In another embodiment, the cell suspension is obtained from a rodent.

In another embodiment, the cell suspension is obtained from spleen tissue, bone marrow tissue, tumour or blood.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

In FIG. 1, the large grey circles represent particles and the smaller black ovals represent a linking moiety such as biotin. (A) and (B) show TAC-mediated direct or indirect linkage of a target cell and particle. (C) and (D) show an antibody (directly or indirectly) conjugated to particle binding a (modified or unmodified) target cell-specific antibody. (E) shows a target cell-specific antibody directly conjugated to a particle. (F) shows a streptavidin:biotin-type indirect linkage of a particle to a target cell-specific antibody.

6

Figure 8:
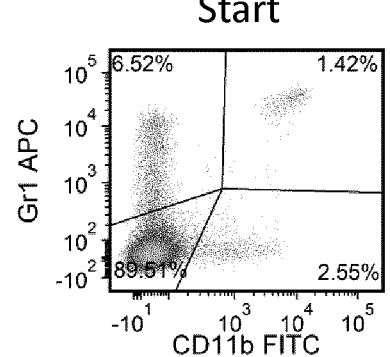
Figure 8:
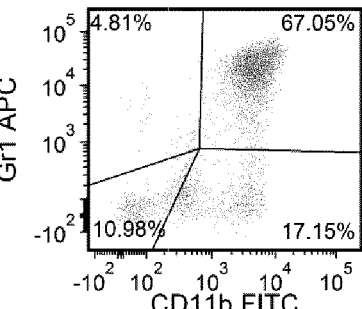

FIG. 8 shows (A) a cocktail of biotinylated antibodies used for negative selection (CD8, Ter119, CD49b, CD19, CD11c, TCRg/d, CD24, TCRa/b, CD4, CD5, CD2, cKit and CD31 antibodies) and (B) CD11b+GR1+ cells in the spleen of a naïve mouse before isolation (start) and after isolation using a direct method ofisolation.

Figure 9:
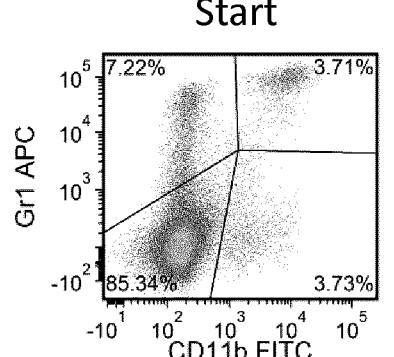
Figure 9:
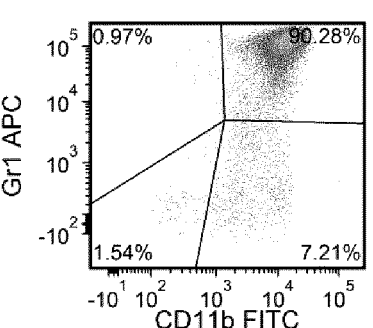

FIG. 9 shows (A) a cocktail of biotinylated antibodies used for negative selection (CD8, B220 (CD45R), Ter119, CD49b, CD19, CD11c, TCRg/d, TCRa/b, CD4, CD5, CD2, cKit and CD31 antibodies) and (B) CD11b+GR1+ cells in the spleen of a naïve mouse before isolation (start) and after isolation using a direct method of isolation.

Figure 10:
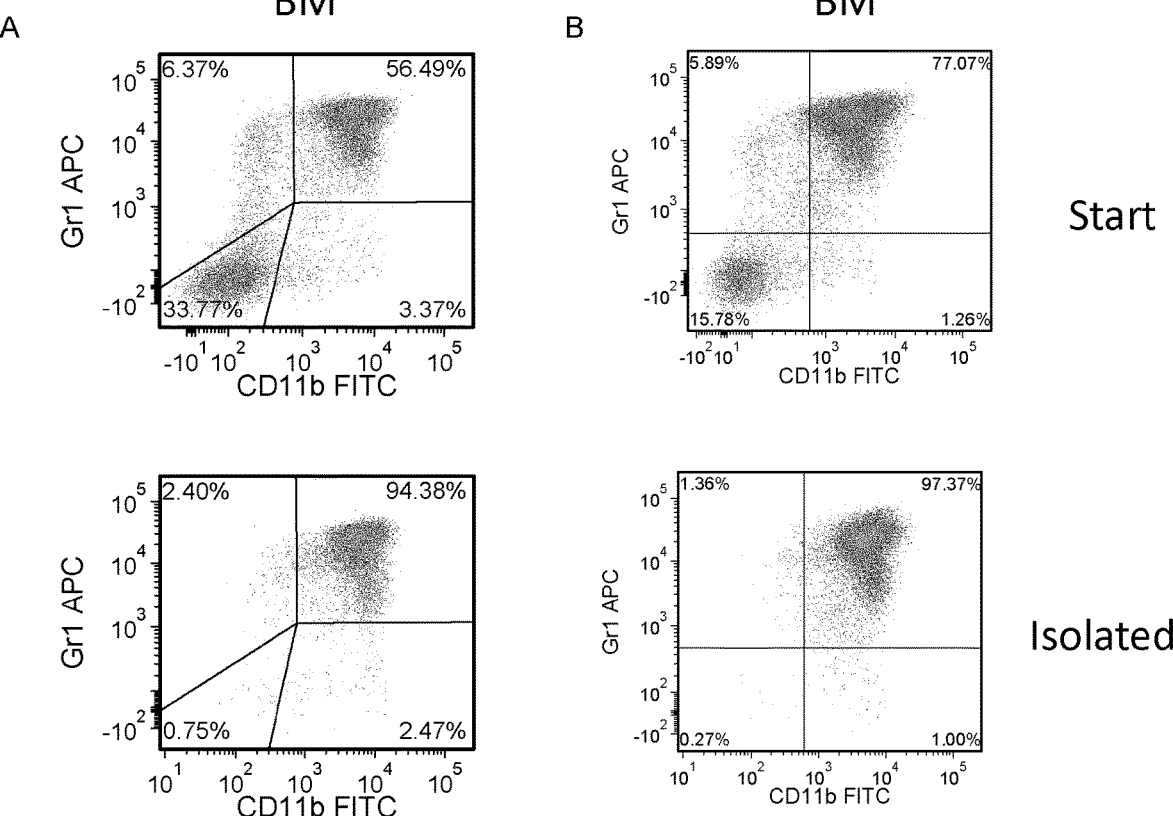

FIG. 10 shows CD11b+GR1+ cells in the BM of a naïve mouse before isolation (start) and after isolation using a direct method of isolation with the cocktail of biotinylated antibodies in cocktail version 6 (A) and 8 (B).

Figure 11:
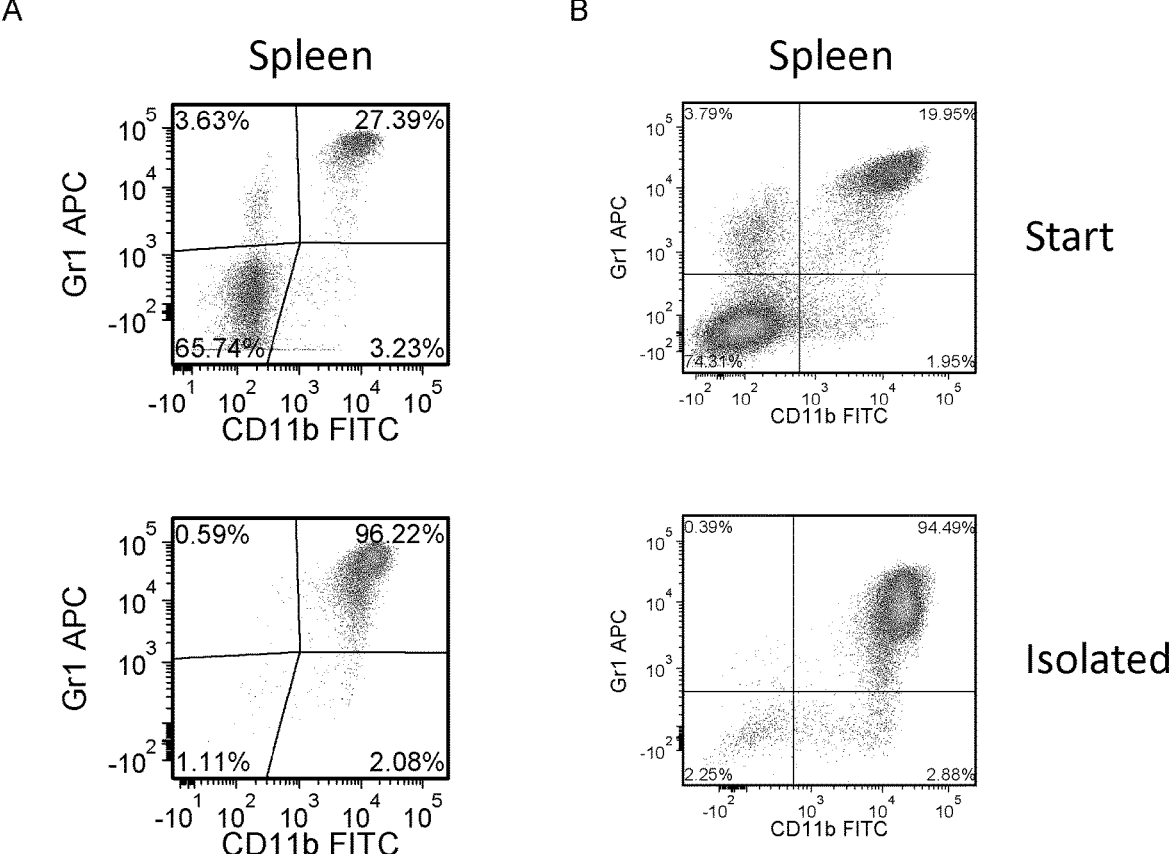

FIG. 11 shows CD11b+GR1+ cells in the spleen of a tumor-bearing mouse before isolation (start) and after isolation using the direct method of isolation with the cocktail of biotinylated antibodies in cocktail version 6 (A) and 8 (B).

Figure 12:
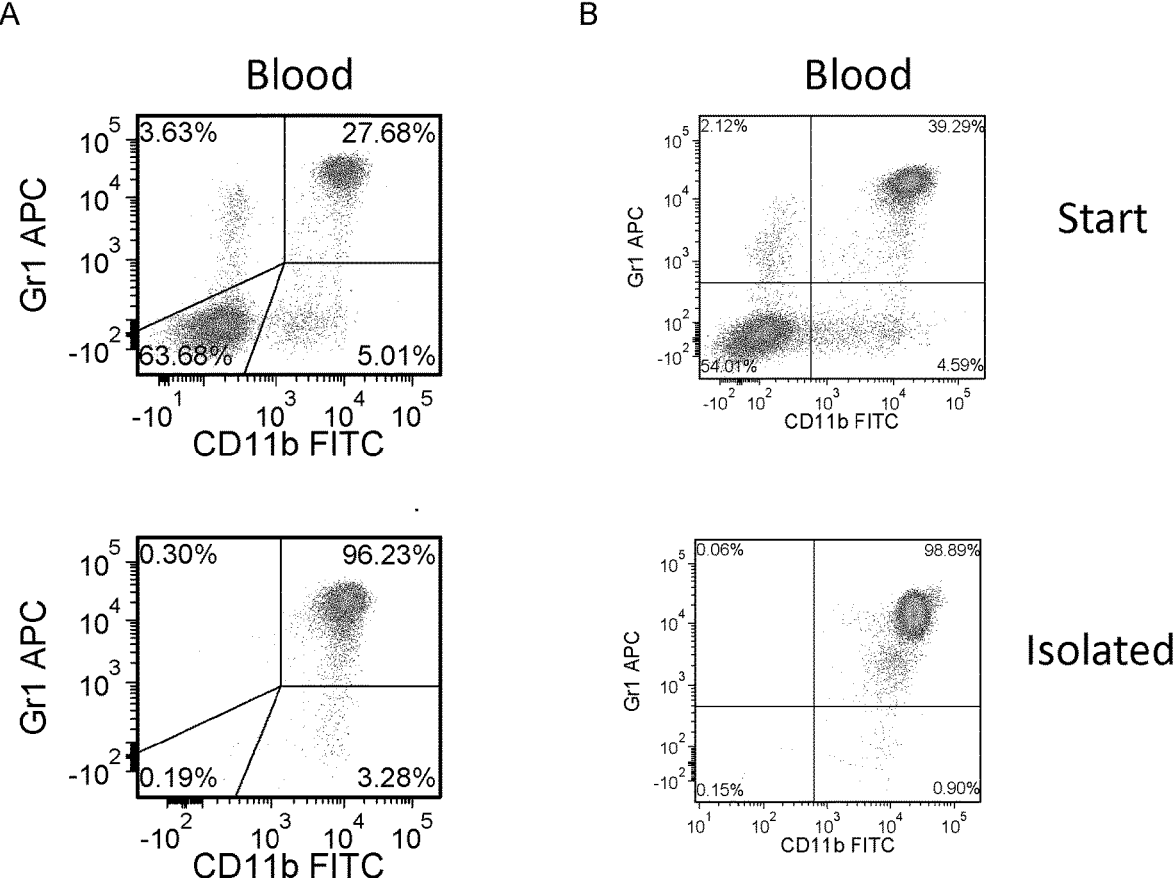

FIG. 12 shows CD11 b+GR1+ cells in the blood of a tumor-bearing mouse before isolation (start) and after isolation using the direct method of isolation with the cocktail of biotinylated antibodies in cocktail version 6 (A) and 8 (B).

Figure 13:
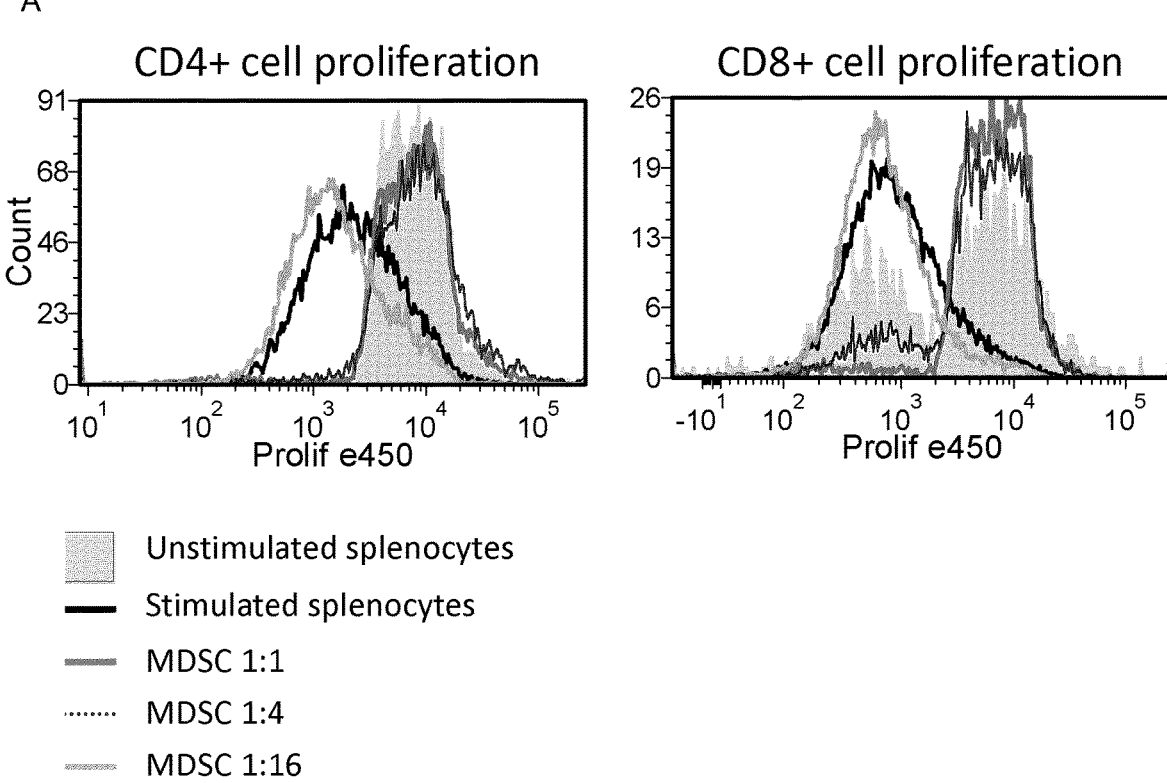
Figure 13:
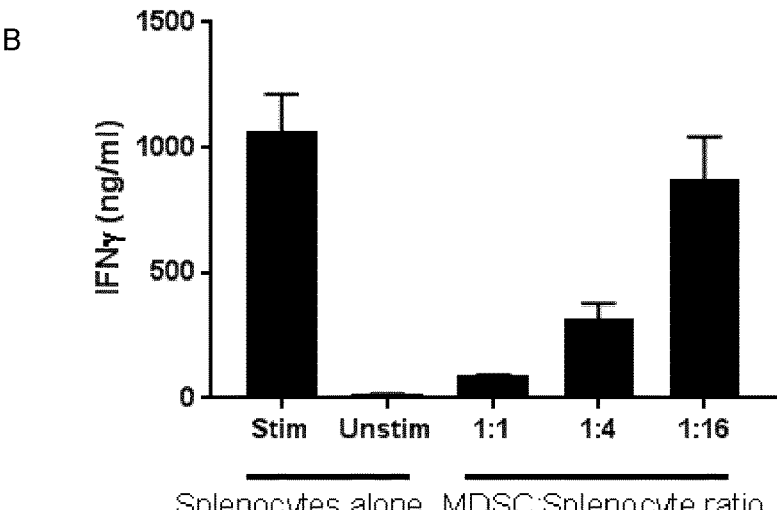

FIG. 13 shows (A) a dose dependent effect of MDSCs on the proliferation of both CD4 and CD8 T cells and (B) a dose dependent effect of MDSCs on IFNg suppression (FIG. 13B).

DETAILED DESCRIPTION

The disclosure describes kits, compositions and methods for isolating or enriching MDSCs from a sample comprising target cells and MDSCs.

As used herein, the term "myeloid-derived suppressor cells" or "MDSCs" refers to a heterogenous group of immune cells from the myeloid lineage. MDSCs are a population of blood cells that regulate immune responses in cancer, chronic infections and inflammatory conditions. Various antigenic or epitopic signatures of MDSCs have been proposed in the literature. By way of non-limiting example, such antigenic or epitopic signatures may include one or more of: (a) for mouse MDSC: CD11b, Gr1, Ly6G, Ly6C, Cd1d, CD16, CD32, CD54, CD86, CD80, CD115, F4/80, CD124, CCR2, CX3CR1 and VEGFR1/2; and (b) for human MDSC: CD11b, CD14, CD15, CD33, CD66b, CD124, VEGFR1, CXCR4, CCR2, CXCR2, CD39, CD80, CD115, CD124 and VEGFR1/2.

In one embodiment, a mouse MDSC may be characterized by a CD11 b$^+$Ly6C$^{lo}$Ly6G$^{hi}$ immunophenotype, a CD11b$^+$Ly6C$^{hi}$Ly6G$^-$ immunophenotype or a CD11b$^+$Gr1$^+$ immunophenotype. In another embodiment, a human MDSC may be characterized by a CD11b$^+$CD33$^+$CD14$^-$CD15$^+$CD66b$^+$ or a CD11b$^+$CD33$^+$CD14$^+$CD15$^-$ HLA-DR$^{lo}$ immunophenotype.

As used herein, the term "target cells" refers to those cells presenting a certain antigen, or epitope thereof, which are targeted by the kits, compositions and methods of this disclosure in the form of a composition, for example a composition as described herein. In such an embodiment, each antibody or fragment thereof may be present in the composition in an amount of about 1-100 µg/ml, or about 2-75 µg/ml, or about 5-50 µg/ml.

In one embodiment, the one or more antibodies comprise a first linkage moiety. The linkage moiety allows for the antibody to be linked, directly or indirectly, to a particle as described in detail herein. In one embodiment, the first linkage moiety is spaced apart from the antigen-binding sites of the one or more antibodies or fragments thereof.

In some embodiments, the first linkage moiety comprises a modification of the one or more antibodies, wherein the modification facilitates the direct or indirect linkage of each of the antibodies to a particle. In one embodiment, the one or more antibodies are modified to comprise one or more biotin groups. In another embodiment, the one or more antibodies are modified to include a polymer, such as a polyethylene glycol (PEG) or a dextran, or derivatives thereof. In another embodiment, the one or more antibodies are modified to comprise avidin or streptavidin.

In another embodiment, the first linkage moiety comprises a site on each of the one or more antibodies capable of being bound by an isotype-specific antibody. In a specific example of such an embodiment, the one or more antibodies may be raised in a first species and via the first linkage moiety may be bound by an antibody raised in a second species.

The kit also comprises a plurality of particles, wherein the plurality of particles are linked or linkable to at least one of the one or more antibodies or fragments thereof.

As used herein, the term "particles" refers to any substance that may tag or label a target cell, whether directly or indirectly, and may facilitate the separation or isolation of such tagged or labelled target cell from a sample comprising target cells, and MDSCs. The particles may be of any composition, size, or density, provided they are amenable to direct or indirect linkage to a target cell (via the antibodies described above) and facilitating the separation or isolation of tagged or labelled target cells.

In one embodiment, the plurality of particles are magnetic or magnetizable. Such particles are well known in the art and are sold by companies such as STEMCELL Technologies, Dynal, Invitrogen, Chemicell, IBA/Stage, SepMag, Advanced magnetics, Immunivest, Kellbenx and BioE Inc. Magnetic or magnetizable particles may facilitate the separation of target cells from a sample when exposed to a magnetic field, such as in immunomagnetic separation processes.

In some embodiments, the plurality of particles have a density within a density range of the one or more target cells. Different types of such particles can facilitate various modes of separating target cells from a sample. For example, a particle having a density within a density range of the one or more target cells may be used in cell separation by sedimentation. In another example, such particles may be magnetic or magnetizable and used in immunomagnetic separation.

In other embodiments, the plurality of particles have a density outside a density range of the one or more target cells. In embodiments where the density of the plurality of particles is outside the density range of the one or more target cells, the plurality of particles may either be more dense than the target cells or less dense than the target cells. For example, particles that are more dense than the target cells may be used in conjunction with a density gradient medium, or to influence the sedimentation rates of target cell:particle complexes in a solution. Alternatively, particles that are less dense than the target cells may also be used in conjunction with a density gradient medium, or to influence the sedimentation rates of target cell: particle complexes in a solution. In a particular embodiment of particles having a density less than a density range of the target cell, such particles either alone or when complexed with target cells may be buoyant.

In one embodiment, the plurality of particles comprise a second linkage moiety. The second linkage moiety can take any form provided it is directly or indirectly linked or linkable to the first linkage moiety.

In one embodiment, the second linkage moiety is conjugated, coated, or otherwise combined with the plurality of particles. In such an embodiment the second linkage moiety may be selected from any known composition capable of being combined with the plurality of particles.

In one embodiment, the second linkage moiety is a coating such as a polymeric coating or any modification, derivative, or analogue thereof. Such a polymeric coating may comprise dextran or PEG, or any modification, derivative, or analogue thereof.

In another embodiment, the second linkage moiety is a protein coating. Examples of proteins that may be used to coat the plurality of particles include, but are not limited to, avidin or streptavidin.

In a still further embodiment, the coating is a molecule such as a vitamin, or a modification, derivative, or analogue thereof. For example, the vitamin may be biotin, or a modification, derivative, or analogue thereof.

As described above, in one embodiment, the plurality of particles comprise a second linkage moiety directly or indirectly linked or linkable to the first linkage moiety (of the one or more antibodies). Accordingly, the second linkage moiety and first linkage moiety cooperate to connect the plurality of particles and the target cells, and more particularly to link the plurality of particles to at least one of the one or more antibodies.

In one embodiment of the kit, the plurality of particles are pre-linked to at least one of the one or more antibodies or fragments thereof, which linkage may be stable or reversible. In such an embodiment it may be desirable that a respective one of the plurality of particles is pre-linked with more than one of the one or more antibodies or fragments thereof. In one embodiment of the kit, the plurality of particles are provided separately from the one or more antibodies, however, prior to use in separation or enrichment processes, the plurality of particles and one or more antibodies are pre-linked, which linkage may be stable or reversible.

In another embodiment, the plurality of particles are coupled to the one or more antibodies in situ. In such an embodiment, the plurality of particles and the one or more antibodies are combined with the sample and these components assemble in situ to form target cell:particle complexes held together through the cooperation of the first linkage moiety of the one or more antibodies and the second linkage moiety of the particles. Variations of such an embodiment may comprise adding the one or more antibodies to the sample prior to the plurality of particles, vice versa, or both at the same time.

Regardless of how the target cell:particle complexes form, the following non-exhaustive examples of specific forms of target cell:particle complexes are all contemplated in this disclosure. Each such complex necessarily relies on the cooperation of the first linkage moiety and the second linkage moiety to bring the target cell:particle complex together.

Figure 1:
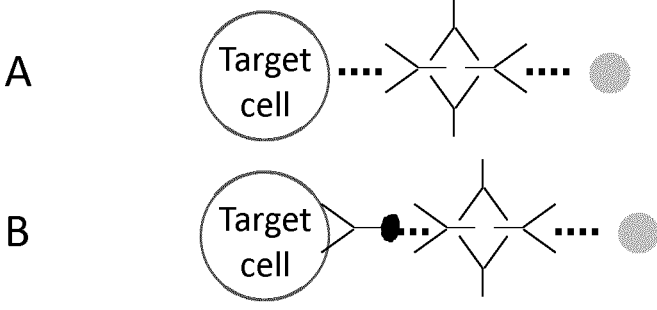
FIG. 1 shows a schematic illustrating various methods, (A) to (F), described herein for targeting a cell for separation.
Figure 1:
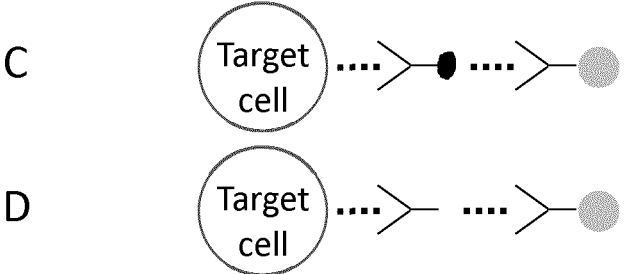

In one embodiment, at least one of the one or more antibodies is directly linked or linkable to the plurality of particles (this arrangement is exemplified, for example, in FIG. 1E). In such a scenario, the one or more antibodies comprise the first linkage moiety and a conjugation partner comprises the second linkage moiety. In such an embodiment, the second linkage moiety is optionally a functional group comprised in the plurality of particles. Indeed, the conjugation of antibodies to particles is well known in the art.

In another embodiment, the one or more antibodies include a modification which interacts with a complementary coating of the plurality of particles. In such a scenario, the first linkage moiety comprises the modification of the one or more antibodies (for example, biotinylation of the one or more antibodies) and the second linkage moiety comprises the coating of the plurality of particles (this arrangement is exemplified, for example, in FIG. 1F). In a specific embodiment, the interaction between the first and second linkage moieties exploits the affinity of biotin for avidin or streptavidin.

In another embodiment, the plurality of particles is conjugated to one or more antibodies which bind the (target cell-specific) one or more antibodies comprising a first linkage moiety (also referred to herein as "particle-conjugated antibodies"). In such a scenario (also depicted for example in FIGS. 1C and 1D), the first linkage moiety may comprise the site where the one or more antibodies are bound by the particle-conjugated antibodies, and the second linkage moiety may comprise either the site of conjugation or the antigen-binding regions of the particle-conjugated antibodies. In a specific embodiment, the one or more antibodies are modified, such as to include a polymer, protein, or some other modification, and the particle-conjugated antibody binds the modification. By way of non-limiting example, the one or more antibodies may be modified by a biotin group, avidin/streptavidin, or a polymer such as PEG or dextran, and the particle-conjugated antibody would bind such modification. In another specific embodiment, the one or more antibodies corresponds to a first isotype and the particle-conjugated antibodies is an anti-isotype antibody. By way of non-limiting example, the one or more antibodies may correspond to mouse IgG1 while the particle-conjugated antibodies may correspond to anti-mouse IgG1.

In another embodiment, the plurality of particles are coated or otherwise modified and at least some of the one or more antibodies are comprised in an antibody complex or composition, wherein the antibody complex or composition includes a first antibody that binds the target cells and a second antibody (for example, a particle-specific antibody) that binds the coating or modification of the particle. In such a scenario, the first linkage moiety comprises the second antibody and the second linkage moiety comprises the coating or modification of the particle.

In another embodiment, the target cell-specific antibody and the particle-specific antibody of the antibody complex or composition are directly conjugated to one another using techniques known in the art. By way of non-limiting example, the particle-specific antibody may recognize a polymer (such as PEG or dextran), protein (such as avidin or streptavidin), or other molecule (such as biotin) used to coat the plurality of particles.

In another specific embodiment, the one or more antibodies, or fragments thereof, are included in a tetrameric antibody complex (TAC) comprising (a) the one or more antibodies, or fragments thereof comprising a first linkage moiety and (b) at least one second antibody (for example, a particle-specific antibody) that is linked or linkable to one or more particles, wherein the one or more antibodies and the at least one second antibody are linked by linker antibodies that bind both the one or more antibodies and the at least one second antibody (this arrangement is exemplified, for example in FIG. 1A). By way of non-limiting example, the particle-specific antibody may recognize a polymer (such as PEG or dextran), protein (such as avidin orstreptavidin), or other molecule (such as biotin) used to coat the plurality of particles. Thus, the plurality of particles are indirectly linked or linkable to the one or more antibodies.

In one example of such an embodiment, the linker antibodies bind the Fc regions of the one or more antibodies, or fragments thereof, and at least one of the second antibody. For example, the one or more antibodies and the at least one of the second antibody may be from a first species, and the linker antibodies may be from a second species. Accordingly, in such an embodiment, the first linkage moiety comprises the Fc regions of the one or more antibodies or fragments thereof and the at least one second antibody or the antigen-binding site thereof.

In another embodiment, the kit comprises (i) one or more antibodies and/or fragments thereof that bind one or more target cells, the one or more antibodies and/or fragments thereof comprising a first linkage moiety, (ii) a plurality of particles comprising a second linkage moiety and (iii) a tetrameric antibody complex (TAC) comprising (a) a first antibody that finds to the first linkage moiety and (b) a second antibody (for example, a particle-specific antibody) that binds to the second linkage moiety, wherein the first antibody and the second antibody are indirectly linked (this arrangement is exemplified, for example in FIG. 1B). The first and second antibodies are optionally linked by linker antibodies, for example linker antibodies that bind the Fc regions of the first and second antibodies. This arrangement is exemplified, for example, in FIG. 1B.

In one embodiment, the kits further comprise blocking agents that block the unintended binding of the Fc portions of the one or more antibodies by Fc receptors on certain cells. For example, Fc receptors are expressed on B cells, monocytes/macrophages, NK cells, granulocytes, mast cells, and dendritic cells. The Fc receptors bind the Fc portion of an antibody and if not blocked can, in the context of cell isolation, lead to non-specific binding and isolation of non-target cells. Examples of blocking agents that may be used in the present kits include, but are not limited to, 5% rat serum, a universal Fc blocking peptide reagent (such as Fc Receptor Block sold by Innovex Biosciences) and blocking antibodies such as antibodies directed against CD16/32.

Compositions

The present disclosure also provides a composition for isolating or enriching MDSC from a sample comprising target cells and MDSC. In one embodiment, the composition comprises at least two, at least 3, at least 4, at least 5, at least 6, at least 7 or at least 8 antibodies or fragments thereof, wherein each antibody or fragment thereof binds a different antigen (or epitope thereof) on the same or different target cell selected from the group consisting of: B cells, T cells, NK cells, dendritic cells, monocytes/macrophages, basophils, mast cells, platelets, endothelial cells, granulocytes or red blood cells and any subtype or progenitor thereof.

In another embodiment, the composition comprises, consists of, or consists essentially of, antibodies or fragments thereof that bind:

(a) T cells, B cells, red blood cells, granulocytes, dendritic cells, and NKcells, (b) T cells, B cells, red blood cells, granulocytes, dendritic cells, NK cells and macrophages, (c) T cells, B cells, red blood cells, granulocytes, dendritic cells, NK cells, macrophages, mast cells and hematopoietic progenitors, (d) T cells, B cells, red blood cells, granulocytes, dendritic cells, NK cells, mast cells and hematopoietic progenitors, or (e) T cells, B cells, red blood cells, dendritic cells, NK cells, macrophages, mast cells, hematopoietic progenitors, monocytes, granulocytes and endothelial cells.

In one embodiment, the composition comprises, consists of, or consists essentially of, antibodies or fragments thereof that bind: CD8, B220 (CD45R), Ter119, CD49b, CD19, CD11c, TCRg/d, CD24, TCRa/b and CD4.

In another embodiment, the composition comprises, consists of, or consists essentially of, antibodies or fragments thereof that bind: CD8, B220 (CD45R), Ter119, CD49b, CD19, CD11c, TCRg/d, CD24, TCRa/b, CD4 and CD5.

In another embodiment, the composition comprises, consists of, or consists essentially of, antibodies or fragments thereof that bind: CD8, B220 (CD45R), Ter119, CD49b, CD19, CD11c, TCRg/d, CD24, TCRa/b, CD4, CD5 and F480.

In another embodiment, the composition comprises, consists of, or consists essentially of, antibodies or fragments thereof that bind: CD8, B220 (CD45R), Ter119, CD49b, CD19, CD11c, TCRg/d, CD24, TCRa/b, CD4, CD5, F480, CD2 and cKit.

In another embodiment, the composition comprises, consists of, or consists essentially of, antibodies or fragments thereof that bind: CD8, B220 (CD45R), Ter119, CD49b, CD19, CD11c, TCRg/d, CD24, TCRa/b, CD4, CD5, CD2 and cKit.

In another embodiment, the composition comprises, consists of, or consists essentially of, antibodies or fragments thereof that bind: CD8, B220 (CD45R), Ter119, CD49b, CD19, CD11c, TCRg/d, CD24, TCRa/b, CD4, CD5, CD2, cKit and CD31.

In another embodiment, the composition comprises, consists of, or consists essentially of, antibodies or fragments thereof that bind: CD8, Ter119, CD49b, CD19, CD11c, TCRg/d, CD24, TCRa/b, CD4, CD5, CD2, cKit and CD31.

In another embodiment, the composition comprises, consists of, or consists essentially of, antibodies or fragments thereof that bind: CD8, B220 (CD45R), Ter119, CD49b, CD19, CD11c, TCRg/d, TCRa/b, CD4, CD5, CD2, cKit and CD31.

A person of skill in the art can readily ascertain the appropriate amount of each antibody or fragment thereof to include in the composition. In some cases the amount of each antibody or fragment thereof included in the composition positively correlates with the amount of antigen and/or the number of a specific type of target cell present in a sample. In some cases, target cells that present a relatively low level of antigen may nonetheless require a relatively high amount of antibody in order to efficiently bind and deplete such target cell(s) from the sample. For example, each antibody or fragment thereof may be present in the composition in an amount of about 1-100 μg/ml, or about 2-75 μg/ml, or about 5-50 μg/ml.

The compositions optionally further comprise blocking agents that block unintended binding of the Fc portions of the one or more antibodies by Fc receptors on certain cells. Examples of blocking agents that may be used in the present compositions include, but are not limited to, 5% rat serum, a universal Fc blocking peptide reagent (such as Fc Receptor Block sold by Innovex Biosciences) and blocking antibodies such as antibodies directed against CD16/32.

In one embodiment, the composition is an aqueous solution. In another embodiment, the composition further comprises a buffer, excipient and/or stabilizer. For example, in particular embodiments, the composition further comprises PBS, Tris, PEG, carboxymethylcellulose, Tween and/or BSA.

Methods

In another aspect, this disclosure provides methods for isolating or enriching MDSCs from a sample comprising target cells and MDSCs. The MDSCs may be isolated or enriched in accordance with the methods described below.

As used herein, the term "sample" refers to a suspension of cells obtained by processing a tissue or blood specimen. The tissue specimen may correspond to any tissue from any creature that may comprise or produce MDSCs. In one embodiment, the tissue or blood specimen is obtained from a human. In another embodiment, the tissue or blood specimen is obtained from any animal, including but not limited to a rodent such as a mouse. In one embodiment, the sample is a tissue or blood specimen obtained from a subject having a condition characterized by MDSCs, such as a tumour specimen.

In one embodiment, the suspension of cells is a single cell suspension cleared or substantially cleared of cellular debris, other debris that may be comprised in cells, and/or non-nucleated cells. The sample may be procured commercially, by way of gift or collaboration, or by the party practicing the methods of this disclosure. In any event, the skilled person will know how to obtain and handle the tissue or blood specimen in order to yield a sample comprising target cells and MDSCs.

Having obtained the tissue or blood specimen from a subject having a condition characterized by MDSCs, whether suppressive or not, the skilled person should timely begin processing the tissue or blood specimen. If the skilled person is unable to timely begin processing the tissue or blood specimen, the tissue or blood specimen should be sufficiently preserved until such later time that the processing may be carried out.

Processing the tissue or blood specimen to yield a sample may be carried out in any way known to the skilled person. For example, the sample may be prepared by manual, mechanical, or enzymatic homogenization, or any combination thereof. Manual homogenization may comprise one or both of a mortar and pestle or mashing a tissue through a filter having an appropriate mesh size, such as 40 or 70 uM. In some embodiments, successive filtration using different mesh sizes may improve the quality of the sample. In another example, the skilled person may use a mechanical homogenizer, such as a tissue dissociator. Various mechanical homogenizers are commercially available. Certain mechanical homogenizers may work in conjunction with enzyme-containing buffers to improve the breakdown of components in the tissue. In another example, an enzymatic buffer may be used independent of the synergistic effects of manual or mechanical homogenization.

While processing the tissue or blood specimen to yield a sample, care should be taken to minimize or avoid damaging the cells therein. In particular, excessive enzymatic or other homogenization may cleave or damage cell surface receptors or other antigens, orepitopes thereof, present on the surface of a cell.

After preparing a sample from the tissue or blood specimen of interest, the kits and compositions of this disclosure may be used in negative selection methods of separating or enriching MDSC and any subset or progenitor thereof.

In one embodiment of the present disclosure, MDSCs (including any subset or progenitor thereof) are separated from a sample comprising target cells and MDSCs, by the binding of one or more target cells to the one or more antibodies, or fragments thereof, of the kits and compositions described above. Depending on the nature of the antibodies and particles, a corresponding target cell:particle complex may form. In such methods of cell separation, the target cells are cells other than the MDSCs (including any subset or progenitor thereof), and thus the target cells (including any subset or progenitor thereof) may be separated from the MDSCs and any other non-target cells in the sample. Accordingly, the one or more antibodies or fragments thereof that bind the one or more target cells are capable of binding an antigen, or epitope thereof, present on the target cells. Such methods are described as "negative selection" methods. One advantage of negative selection methods is that "untouched" MDSCs (i.e. those not coupled any antibodies) are obtained.

Depending on the type of sample and the cell types included therein, or on the purity levels desired in a negative selection method of enriching MDSCs from a sample comprising target cells and MDSCs, the types of cells targeted by the one or more antibodies is an important consideration. Correspondingly, the kits, compositions and methods of this disclosure contemplate various combinations of antibodies that differ in the types of target cells bound by the one or more antibodies.

In one embodiment, the one or more antibodies or fragments thereof, bind one or more antigens, or epitopes thereof, on the surface of T cells, B cells, red blood cells, granulocytes, dendritic cells, and NK cells.

In another embodiment, the one or more antibodies or fragments thereof, bind one or more antigens, or epitopes thereof, on the surface of T cells, B cells, red blood cells, granulocytes, dendritic cells, NK cells and macrophages.

In another embodiment, the one or more antibodies or fragments thereof, bind one or more antigens, or epitopes thereof, on the surface of T cells, B cells, red blood cells, granulocytes, dendritic cells, NK cells, macrophages, mast cells and hematopoietic progenitors.

In another embodiment, the one or more antibodies or fragments thereof, bind one or more antigens, or epitopes thereof, on the surface of T cells, B cells, red blood cells, dendritic cells, NK cells, macrophages, mast cells, hematopoietic progenitors, monocytes, granulocytes and endothelial cells.

In order to effect the enrichment methods of this disclosure, the sample is contacted with a one or more antibodies or fragments thereof that bind one or more target cells. The contacting step of the disclosed methods, may be carried out in various ways.

In some embodiments, the sample is first contacted with the one or more antibodies or fragments thereof. On the one hand, certain embodiments include only a single contacting step, such as where the one or more antibodies are directly conjugated to the plurality of particles, where the one or more antibodies and the plurality of particles are pre-complexed prior to the contacting step, or where the plurality of particles are allowed to complex with the one or more antibodies in situ. On the other hand, in other embodiments where multiple antibodies mediate the linkage of a target cell and a particle, it may be necessary to include a second antibody contacting step after the first antibody contacting step, for example where an isotype-specific antibody binds a target cell-specific antibody.

Notwithstanding the number of contacting, incubation and/or washing steps that are used in the methods disclosed herein, the methods may nonetheless be considered single-step methods because the target cells are coupled to the particles once. However, the person skilled in the art may have reason, such as to increase purity (possibly at the expense of recovery) of target cells, to perform the methods of this disclosure more than once in succession.

In those embodiments where the sample is first contacted with the one or more antibodies to allow target cell:antibody complexes to form, the sample comprising target cell:antibody complexes may subsequently be contacted with the plurality of particles.

In one embodiment, the amount of each antibody or fragment thereof used in the presently claimed methods positively correlates with the amount of antigen and/or the number of a specific type of target cell present in a sample. In another embodiment, target cells that present a relatively low level of antigen may nonetheless require a relatively high amount of antibody in order to efficiently bind and deplete such target cell(s) from the sample. For example, each antibody or fragment thereof may be used in the presently claimed methods in an amount of about 1-100 μg/ml, or about 2-75 μg/ml, or about 5-50 μg/ml. In another embodiment, the sample is contacted with a composition comprising the one or more antibodies or fragments thereof, for example a composition as described herein.

In another embodiment, the sample is contacted with a composition comprising the one or more antibodies or fragments thereof, for example a composition as described herein.

In one embodiment, the methods of this disclosure may further comprise adding blocking agents that block the unintended binding of the Fc regions of the one or more antibodies by Fc receptors on certain cells. Examples of blocking agents useful in the present methods include, but are not limited to, 5% rat serum, a universal Fc blocking peptide reagent (such as Fc Receptor Block sold by Innovex Biosciences) and blocking antibodies such as antibodies directed against CD16/32. In one embodiment, the blocking agent is added prior to contacting the sample with one ore more antibodies or fragments thereof that bind one or more target cells.

Regardless of the sequence in which the sample is contacted with the one or more antibodies or fragments thereof and the plurality of particles, it may be necessary to perform one or more incubation steps. In embodiments where the sample is first contacted with the one or more antibodies, including pre-complexed particles and antibodies, incubating the target cells and the one or more antibodies under permissive conditions allows the one or more antibodies to bind the target cells and form target cell:antibody complexes. In embodiments where the sample is first contacted with target cell-specific antibodies and then contacted with, for example, isotype-specific antibodies, successive incubation steps under permissive conditions may be carried out to form higher order target cell:antibody complexes.

In embodiments where the one or more antibodies had not been pre-complexed with the one or more antibodies, samples comprising target cell:antibody complexes or higher order target cell:antibody complexes may be contacted with the one or more antibodies. Incubating such target cell:antibody complexes and the plurality of particles under permissive conditions allows the formation of target cell:particle complexes, via the respective first linkage moiety and the second linkage moiety.

Following any incubation step but prior to a subsequent contacting step it may be desirable to wash or purify the sample. For example, antibodies that remain unbound to target cells or to target-specific antibodies may be removed from the sample by, for example, pelleting the cells therein, particularly in those cases where the unbound antibodies may interfere with subsequent steps of the methods disclosed herein.

Once target cell:particle complexes have formed, the sample may be subjected to any appropriate separation process. In one embodiment, the desired cells (in this case the MDSCs or any subset or progenitor thereof) are contained in the solution that is poured-off or aspirated.

In one embodiment, the MDSCs may be enriched by immunomagnetic separation. In such case, the particles of the target cell:particle complexes are magnetic or magnetizable, and exposing the target cell:particle complexes to a magnetic field enables the retention thereof in proximity to the magnetic field. In one embodiment, the target cell: particle complexes are retained in proximity to the magnetic field and the MDSC would remain in solution. Thus, pouring-off or aspirating the solution separates the MDSCs from the target cells and particles to yield a solution comprising pure or substantially pure MDSCs.

In another embodiment, the MDSCs may be enriched by sedimentation.

In another embodiment, the MDSCs may be enriched on the basis of density. In a specific embodiment the particles are buoyant. In such an embodiment, the target cell:particle complexes may rise to or near to the top of the sample. Such target cell:particle complexes may be selectively removed from the sample. In a different embodiment, the particles may be more dense than a density range of the target cells. In such an embodiment, the target cell:particle complexes may sink to or near to the bottom of the sample. Such target cell:particle complexes may be selectively removed from the sample.

In one embodiment, the methods described herein provide a population of cells enriched for MDSCs.

In one embodiment, the enriched population of cells comprises at least 30%, 35%, 40%, 45%, 50%, 55%, 60%, 65%, 70%, 75%, 80%, 85%, 90%, 95% or 99% MDSCs. In one embodiment, cells are identified as MDSCs by the presence of CD11b and GR1 on the cell surface (CD11b+ GR1+ cells). In another embodiment, mouse cells are identified as MDSCs by the presence of any of the following proteins, or combination thereof, on the cell surface: CD11b, Gr1, Ly6G, Ly6C, Cd1d, CD16, CD32, CD54, CD86, CD80, CD115, F4/80, CD124, CCR2, CX3CR1 and VEGFR1/2. In a further embodiment, mouse cells are identified as MDSCs by the following phenotypes: CD11 b+Ly6C$^{lo}$Ly6G$^{hi}$, CD11b+Ly6C$^{hi}$Ly6G$^-$ or CD11b+Gr1+. In another embodiment, human cells are identified as MDSCs by the presence of any of the following proteins, or combination thereof, on the cell surface: CD11b, CD14, CD15, CD33, CD66b, CD124, VEGFR1, CXCR4, CCR2, CXCR2, CD39, CD80, CD115, CD124 and VEGFR1/2. In another embodiment, human cells are identified as MDSCs by the following phenotypes: CD11b+CD33+CD14-CD15+ CD66b+ or CD11b+CD33+CD14+CD15$^-$HLA-DR$^{lo}$.

In one embodiment, the use of the kits, compositions and methods described herein recover about 20-90%, about 25-85%, about 30-80%, about 35-75%, about 40-70%, about 45-65%, or about 50-60% of the MDSCs present in a sample, such as a naïve or a tumour sample, see Table 1.

In one embodiment of this disclosure the use of the kits, compositions and methods described herein enrich for MDSCs which are functional and may be used in downstream applications. In a preferred embodiment, the functional MDSCs are enriched using kits, compositions and/or methods in a negative selection approach. One example of a test to measure the functionality of MDSCs may include assessing the proliferation of stimulated or unstimulated splenocytes (e.g. a T cell population within the splenocytes) when cultured in the presence of MDSCs. Another test to measure the functionality of MDSCs may include measuring the suppression of IFNg production by splenocytes that are cultured in the presence of MDSCs.

A different aspect of this disclosure contemplates the use of the kits, compositions and methods described herein to enrich for MDSCs from a subject presenting a condition characterized in induced MDSCs, such as cancer, inflammatory conditions like autoimmune disorders, and chronic infection.

The following non-limiting examples are illustrative of the present disclosure:

Example 1: Dissociation of Spleen Tissue to a Single Cell Suspension

Spleens were harvested from euthanized mice in accordance with standard procedures and applicable animal welfare guidelines. Recovered spleens were disrupted by mashing spleens through a 70 μm mesh nylon strainer with frequent rinsing with PBS containing 2% fetal bovine serum (FBS) to yield a cell suspension. Aggregates and other debris were removed by passing the cell suspension through an additional 70 μm mesh nylon strainer. The flow-through was centrifuged at approximately 300×g for 10 minutes and the pelleted cells were resuspended at 1×10$^8$ nucleated cells/ml in PBS containing 2% FBS and 1 mM EDTA.

Example 2: Dissociation of Bone Marrow Tissue to a Single Cell Suspension

Bone marrow (BM) was harvested from euthanized mice in accordance with standard procedures and applicable animal welfare guidelines. BM was recovered by flushing femur and tibia with in PBS containing 2% FBS and 1 mM EDTA using a syringe equipped with a 23-26 gauge needle to yield a cell suspension. Aggregates in the cell suspension were dispersed by gently passing the cell suspension through the syringe several times or through a 70 μm mesh nylon strainer. The homogenate or flow-through was centrifuged at approximately 300×g for 6 minutes and the pelleted cells were resuspended at 1×10$^8$ cells/ml in in PBS containing 2% FBS and 1 mM EDTA.

Example 3: Preparation of a Single Cell Suspension from Peripheral Blood

Peripheral blood was harvested from euthanized mice in accordance with standard procedures and applicable animal welfare guidelines. Red blood cells within harvested peripheral blood were lysed using standard procedures prior downstream use. In particular, red blood cells were lysed by combining one part blood with nine parts ammonium chloride solution, followed by a 15-minute incubation on ice. The lysate was centrifuged at approximately 300×g for 6 minutes and the supernatant was discarded. The cell pellet was washed once with in PBS containing 2% FBS and 1 mM EDTA medium, and centrifuged at approximately 300×g for 6 minutes. The supernatant was discarded and the cell pellet was resuspended at $1 \times 10^8$ cells/ml in in PBS containing 2% FBS and 1 mM EDTA.

Example 4: Direct Method of MDSC Enrichment

Prior to commencing enrichment of the single cell suspension produced in accordance with Examples 1-3, the cells were blocked to prevent non-specific binding of Fc portions of the one or more antibodies to Fc receptors of non-target cells using either the addition of 5% rat serum or antibodies directed against CD16/32.

A mixture of biotinylated antibodies directed against non-MDSC target cells was added to the cell suspension and incubated for 10 mins to label target cells. After this first incubation period, streptavidin coated magnetizable particles were added to the sample at 75-150 ul/ml and incubated for 5 min. After this second incubation, the formed target cell:particle complexes were separated from the sample by placing the sample in proximity to a magnetic field for 3 min. The non-target cells, which were enriched for MDSC, were isolated from the sample by removing the solution while continuing to expose the sample to the magnetic field.

Example 5: Indirect Method of MDSC Enrichment

Prior to commencing enrichment of the single cell suspension produced in accordance with Examples 1-3, the cells were blocked to prevent non-specific binding of Fc portions of the one or more antibodies to Fc receptors of non-target cells using either the addition of 5% rat serum or antibodies directed against CD16/32.

A mixture of biotinylated antibodies directed against non-MDSC target cells was added to the cell suspension and incubated for 10 mins to label target cells. After this first incubation period, tetrameric antibody complexes (TAC) were added to the sample. The TAC consisted of an anti-biotin antibody and an anti-dextran antibody held in a tetrameric array by two linker antibodies directed against the Fc regions of the anti-biotin and anti-dextran antibodies. After addition of the TAC, the sample was incubated to allow formation of complexes comprising target cells, biotin-conjugated antibodies, and TAC by incubating for 10 min at room temperature. After this second incubation period, dextran-coated magnetizable particles were added to the sample at 50-150 ul/ml and incubated for 5 min at room temperature. After this third incubation period, the formed complexes comprising target cells, biotin-conjugated antibodies, TAC, and particles were separated from the sample by placing the sample in proximity to a magnetic field for 3 min. The non-target cells, which were enriched for MDSC, were isolated from the sample by removing the solution while continuing to expose the sample to the magnetic field.

Example 6: Indirect Method of MDSC Enrichment

Prior to commencing enrichment of the single cell suspension produced in accordance with Examples 1-3, the cells were blocked to prevent non-specific binding binding of Fc portions of the one or more antibodies to Fc receptors of non-target cells using either the addition of 5% rat serum or antibodies directed against CD16/32.

A mixture of biotinylated antibodies (also referred to herein as a "cocktail") directed against non-MDSC target cells was premixed and incubated for 5 min with an anti-isotype TAC to allow formation of complexes comprising target cell-specific antibodies, and TAC. The TAC consisted of a combination of mouse monoclonal antibodies directed against the rat IgG2a, IgG2b, rat IgM and Armenian hamster IgG isotype specific antibodies contained in the target cell-specific antibody mixture and an anti-dextran antibody held in a tetrameric array by two linker antibodies directed against the Fc regions of the anti-biotin and anti-dextran antibodies. After addition of the antibody+TAC mixture to the cells, the sample was incubated for 10 min to allow formation of complexes comprising target cells, target cell-specific antibodies, and TAC. After this incubation period, dextran-coated magnetizable particles were added to the sample at 25-100 ul/ml and incubated for 3 min. After this second incubation period, the formed complexes comprising target cells, target cell-specific antibodies, TAC, and particles were separated from the sample by placing the sample in proximity to a magnetic field for 3 min. The non-target cells, which were enriched for MDSC, were isolated from the sample by removing the solution while continuing to expose the sample to the magnetic field.

Example 7: Enrichment of MDSCs from a Spleen Sample Using a First Antibody Cocktail in Direct and Indirect Approaches Cell suspensions were prepared from the spleen of a naïve C57Bl/6 mouse in accordance with Example 1, and enrichment was carried out using the methods outlined in Example 4 and Example 5 or Example 6.

Figure 2:
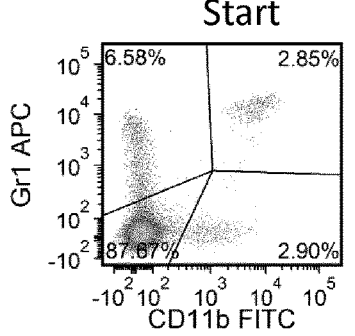
FIG. 2 shows (A) a cocktail of biotinylated antibodies used for negative selection (CD8, B220 (CD45R), Ter119, CD49b, CD19, CD11c, TCRg/d, CD24, TCRa/b and CD4 antibodies) and (B) CD11b+GR1+ cells in the spleen of a naïve mouse before isolation (start) and after isolation using a direct and indirect method of isolation.
Figure 2:
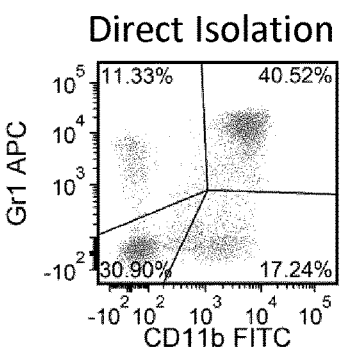
Figure 2:
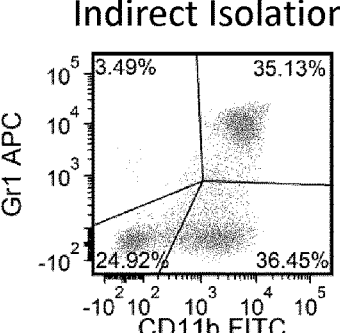

The first cocktail tested contained target-specific biotinylated antibodies directed against antigens present on surfaces of T cells, B cells, red blood cells, granulocytes, dendritic cells, and NK cells. FIG. 2 shows representative flow cytometry plots of MDSC proportions in start spleen cells, and in populations enriched using the first cocktail in either direct or indirect methods. Overall, the first cocktail yielded a mean purity of 38% MDSCs, assessed as CD11b+Gr1+ cells (gated on live CD45+ cells) for the direct method of isolation and 38% for the indirect method of isolation.

Example 8: Enrichment of MDSCs from a Spleen Sample Using a Second Antibody Cocktail in Direct and Indirect Approaches Cell suspensions were prepared from the spleen of a naïve C57Bl/6 mouse in accordance with Example 1, and enrichment was carried out using the methods outlined in Example 4 and Example 5 or Example 6.

Figure 3:
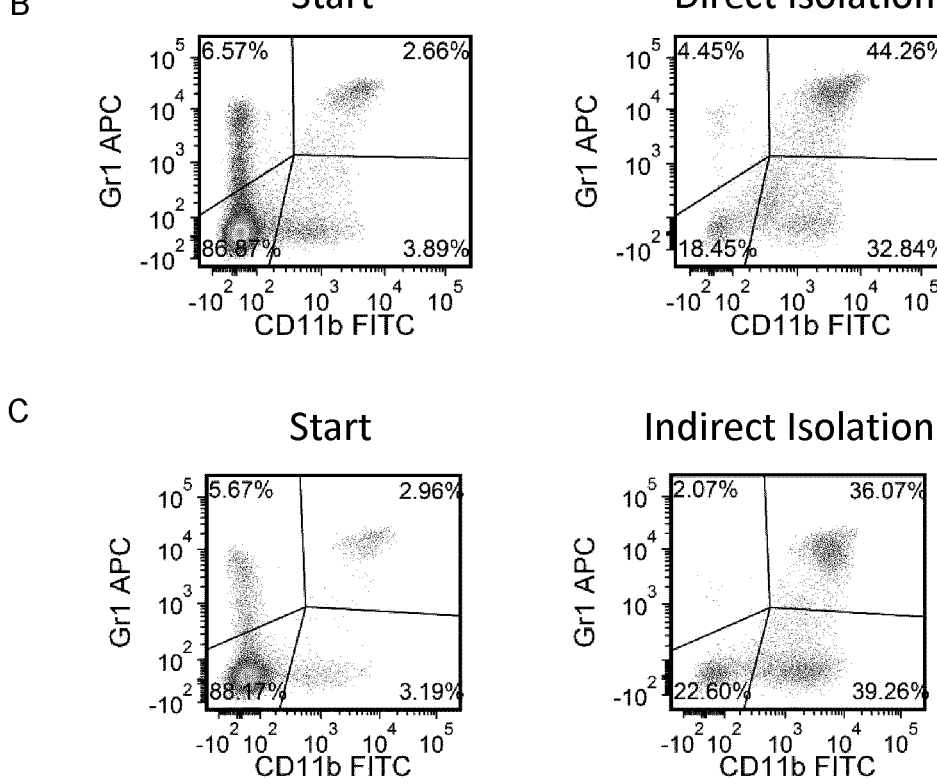
FIG. 3 shows (A) a cocktail of biotinylated antibodies used for negative selection (CD8, B220 (CD45R), Ter119, CD49b, CD19, CD11c, TCRg/d, CD24, TCRa/b, CD4 and CD5 antibodies), (B) CD11b+GR1+ cells in the spleen of a naïve mouse before isolation (start) and after isolation using the direct method of isolation and (C) CD11b+GR1+ cells in the spleen before isolation (start) and after isolation using an indirect method of isolation.

The second cocktail tested contained target-specific biotinylated antibodies directed against antigens present on surfaces of T cells, B cells, red blood cells, granulocytes, dendritic cells, and NK cells. FIG. 3 shows representative flow cytometry plots of MDSC proportions in start spleen cells, and in populations enriched using the second cocktail in either direct or indirect methods. Overall, the second cocktail yielded a mean purity of 52% MDSCs, assessed as CD11 b+Gr1+ cells (gated on live CD45+ cells) for the direct method of isolation and 33% for the indirect method of isolation.

Example 9: Enrichment of MDSCs from a Spleen Sample Using a Third Antibody Cocktail in a Direct Approach Cell suspensions were prepared from the spleen of a naïve C57Bl/6 mouse in accordance with Example 1, and enrichment was carried out using the method outlined in Example 4.

Figure 4:
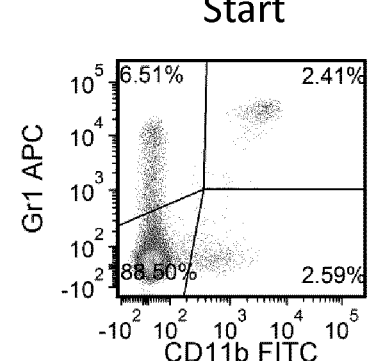
FIG. 4 shows (A) a cocktail of biotinylated antibodies used for negative selection (CD8, B220 (CD45R), Ter119, CD49b, CD19, CD11c, TCRg/d, CD24, TCRa/b, CD4, CD5 and F480 antibodies) and (B) CD11b+GR1+ cells in the spleen of a naïve mouse before isolation (start) and after isolation using a direct method of isolation.
Figure 4:
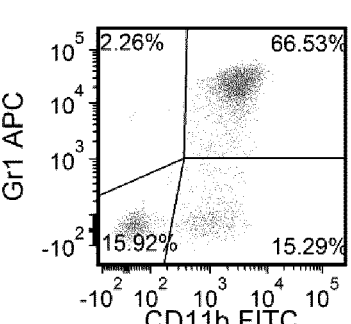

The third cocktail tested contained target-specific biotinylated antibodies directed against antigens present on surfaces of T cells, B cells, red blood cells, granulocytes, dendritic cells, NK cells and macrophages. FIG. 4 shows representative flow cytometry plots of MDSC proportions in start spleen cells and in populations enriched using the third cocktail in a direct method. Overall, the third cocktail yielded a mean purity of 54% MDSCs, assessed as CD11 b+Gr1+ cells (gated on live CD45+ cells) for the direct method of isolation.

Example 10: Enrichment of MDSCs from a Spleen Sample Using a Fourth Antibody Cocktail in a Direct Approach Cell suspensions were prepared from the spleen of a naïve C57BI/6 mouse in accordance with Example 1, and enrichment was carried out using the method outlined in Example 4.

Figure 5:
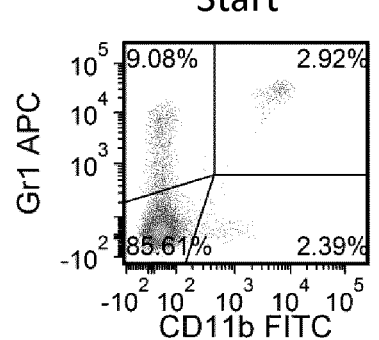
FIG. 5 shows (A) a cocktail of biotinylated antibodies used for negative selection (CD8, B220 (CD45R), Ter119, CD49b, CD19, CD11c, TCRg/d, CD24, TCRa/b, CD4, CD5, F480, CD2 and cKit antibodies) and (B) CD11b+GR1+ cells in the spleen of a naïve mouse before isolation (start) and after isolation using a direct method of isolation.
Figure 5:
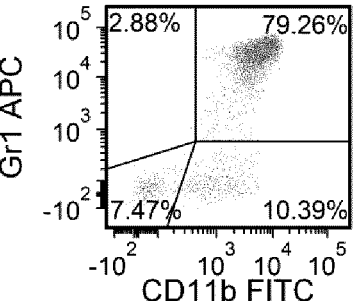

The fourth cocktail tested contained target-specific biotinylated antibodies directed against antigens present on surfaces of T cells, B cells, red blood cells, granulocytes, dendritic cells, NK cells, macrophages, mast cells and hematopoietic progenitors. FIG. 5 shows representative flow cytometry plots of MDSC proportions in start spleen cells and in populations enriched using the fourth cocktail in a direct method. Overall, the fourth cocktail yielded a mean purity of 67% MDSCs, assessed as CD11b+Gr1+ cells (gated on live CD45+ cells) for the direct method of isolation.

Example 11: Enrichment of MDSCs from a Spleen Sample Using a Fifth Antibody Cocktail in a Direct Approach Cell suspensions were prepared from the spleen of a naïve C57BI/6 mouse in accordance with Example 1, and enrichment was carried out using the method outlined in Example 4.

Figure 6:
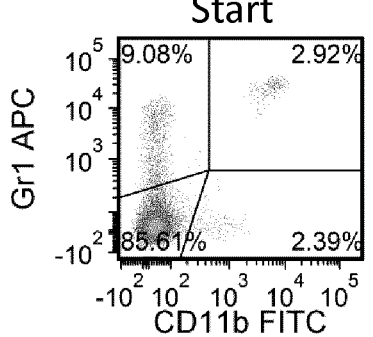
FIG. 6 shows (A) a cocktail of biotinylated antibodies used for negative selection (CD8, B220 (CD45R), Ter119, CD49b, CD19, CD11c, TCRg/d, CD24, TCRa/b, CD4, CD5, CD2 and cKit antibodies) and (B) CD11b+GR1+ cells in the spleen of a naïve mouse before isolation (start) and after isolation using a direct method of isolation.
Figure 6:
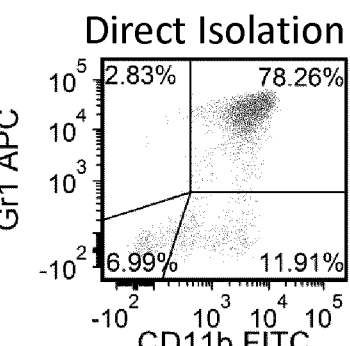

The fifth cocktail tested contained target-specific biotinylated antibodies directed against antigens present on surfaces of T cells, B cells, red blood cells, granulocytes, dendritic cells, NK cells, mast cells and hematopoietic progenitors. FIG. 6 shows representative flow cytometry plots of MDSC proportions in start spleen cells and in populations enriched using the fifth cocktail in a direct method. Overall, the fifth cocktail yielded a mean purity of 72% MDSCs, assessed as CD11b+Gr1+ cells (gated on live CD45+ cells) for the direct method of isolation.

Example 12: Enrichment of MDSCs from a Spleen Sample Using a Sixth Antibody Cocktail in Direct and Indirect Approaches Cell suspensions were prepared from the spleen of a naïve C57BI/6 mouse in accordance with Example 1, and enrichment was carried out using the methods outlined in Example 4 and Example 5 or Example 6.

Figure 7:
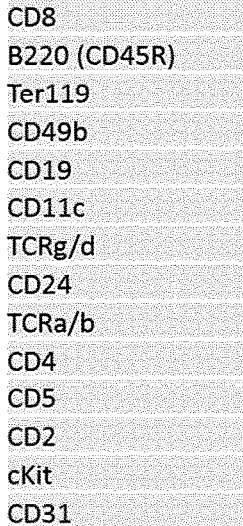
FIG. 7 shows (A) a cocktail of biotinylated antibodies used for negative selection (CD8, B220 (CD45R), Ter119, CD49b, CD19, CD11c, TCRg/d, CD24, TCRa/b, CD4, CD5, CD2, cKit and CD31 antibodies) and (B) CD11 b+GR1+ cells in the spleen of a naïve before isolation (start) and after isolation using a direct method of isolation and using an indirect method of isolation.
Figure 7:
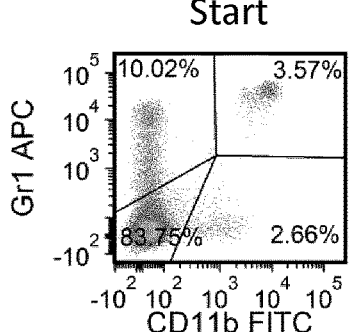
Figure 7:
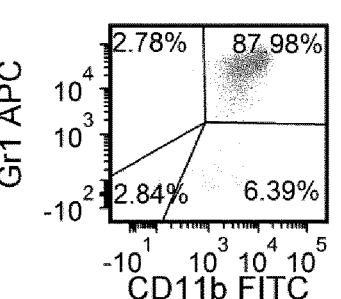
Figure 7:
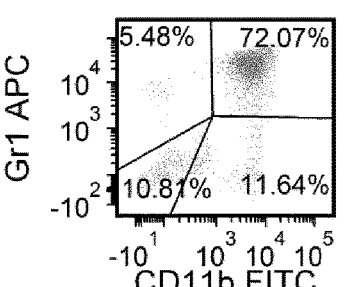

The sixth cocktail tested contained target-specific biotinylated antibodies directed against antigens present on surfaces of T cells, B cells, red blood cells, dendritic cells, NK cells, macrophages, mast cells, hematopoietic progenitors, monocytes, granulocytes and endothelial cells. FIG. 7 shows representative flow cytometry plots of MDSC proportions in start spleen cells, and in populations enriched using the sixth cocktail in either direct or indirect methods. Overall, the sixth cocktail yielded a mean purity of 90% MDSCs, assessed as CD11b+Gr1+ cells (gated on live CD45+ cells) for the direct method of isolation and 68% for the indirect isolation approach.

Example 13: Enrichment of MDSCs from a Spleen Sample Using a Seventh Antibody Cocktail in a Direct Approach Cell suspensions were prepared from the spleen of a naïve C57BI/6 mouse in accordance with Example 1, and enrichment was carried out using the method outlined in Example 4.

The seventh cocktail tested contained target-specific biotinylated antibodies directed against antigens present on surfaces of T cells, B cells, red blood cells, dendritic cells, NK cells, macrophages, mast cells, hematopoietic progenitors, monocytes, granulocytes and endothelial cells. FIG. 8 shows representative flow cytometry plots of MDSC proportions in start spleen cells and in populations enriched using the seventh cocktail in a direct method. Overall, the seventh cocktail yielded a mean purity of 70% MDSCs, assessed as CD11b+Gr1+ cells (gated on live CD45+ cells) for the direct method of isolation.

Example 14: Enrichment of MDSCs from a Spleen Sample Using an Eighth Antibody Cocktail in a Direct Approach Cell suspensions were prepared from the spleen of a naïve C57BI/6 mouse in accordance with Example 1, and enrichment was carried out using the method outlined in Example 4.

The eighth cocktail tested contained target-specific biotinylated antibodies directed against antigens present on surfaces of T cells, B cells, red blood cells, dendritic cells, NK cells, macrophages, mast cells, hematopoietic progenitors, monocytes, some granulocytes and endothelial cells. FIG. 9 shows representative flow cytometry plots of MDSC proportions in start spleen cells and in populations enriched using the eighth cocktail in a direct method. Overall, the eighth cocktail yielded a mean purity of 85% MDSCs, assessed as CD11 b+Gr1+ cells (gated on live CD45+ cells) for the direct method of isolation.

Example 15: Enrichment of MDSCs from a Bone Marrow Sample Using a Direct Approach Cell suspensions were prepared from the bone marrow of a naïve C57BI/6 mouse in accordance with Example 2, and enrichment was carried out using the method outlined in Example 4.

The sixth and eight cocktails tested contained target-specific biotinylated antibodies directed against antigens present on surfaces of T cells, B cells, red blood cells, dendritic cells, NK cells, macrophages, mast cells, hematopoietic progenitor, monocytes, granulocytes and endothelial cells. FIG. 10 shows representative flow cytometry plots of MDSC proportions in start bone marrow cells and in populations enriched using (A) the sixth cocktail in a direct method and (B) the eight cocktail in a direct method. Overall, the sixth cocktail yielded a mean purity of 94% MDSCs and the eight cocktail 96% MDSCs, assessed as CD11 b+Gr1+ cells (gated on live CD45+ cells) for the direct method of isolation.

Example 16: Enrichment of MDSCs from a Spleen
Sample Harvested from a Tumour-Bearing Mouse
in a Direct Approach Cell suspensions were prepared from the spleen of a 4T1
tumor bearing Balb/c mouse in accordance with Example 1,
and enrichment was carried out using the method outlined in
Example 4.

The sixth and eight cocktails tested contained target-
specific biotinylated antibodies directed against antigens
present on surfaces of T cells, B cells, red blood cells,
dendritic cells, NK cells, macrophages, mast cells progenitor
cells, monocytes, some granulocytes and endothelial cells.
FIG. 11 shows representative flow cytometry plots of MDSC
proportions in start spleen cells and in populations enriched
using (A) the sixth and (B) the eight cocktail in a direct
method. Overall, the sixth cocktail yielded a mean purity of
90% MDSCs and the eight cocktail 94%, assessed as
CD11b+Gr1+ cells (gated on live CD45+ cells) for the direct
method of isolation.

Example 17: Enrichment of MDSCs from a Blood
Sample Harvested from a Tumour-Bearing Mouse
in a Direct Approach Cell suspensions were prepared from the blood of a B16
tumor bearing c57BI/6 mouse in accordance with Example
3, and enrichment was carried out using the method outlined
in Example 4.

The sixth and eight cocktail tested contained target-
specific biotinylated antibodies directed against antigens
present on surfaces of T cells, B cells, red blood cells,
dendritic cells, NK cells, macrophages, mast cells progenitor
cells, monocytes, some granulocytes and endothelial cells.
FIG. 12 shows representative flow cytometry plots of
MDSC proportions in start blood cells and in populations
enriched using (A) the sixth cocktail and (B) the eight
cocktail in a direct method. Overall, the sixth cocktail
yielded a mean purity of 93% MDSCs and the eight cocktail
99%, assessed as CD11b+Gr1+ cells (gated on live CD45+
cells) for the direct method of isolation.

Example 18: Isolation of MDSCs (CD11b+Gr1+
Cells) from Spleens Harvested from Naïve and
Tumour-Bearing Mice Using the Eight Antibody
Cocktail in a Direct Approach Cell suspensions were prepared from the spleen of either
naïve C57BI/6 mice of 4T1 tumor bearing Balb/c mouse in
accordance with Example 1, and enrichment was carried out
using the method outlined in Example 4.

The eight cocktail tested contained target-specific bioti-
nylated antibodies directed against antigens present on sur-
faces of T cells, B cells, red blood cells, dendritic cells, NK
cells, macrophages, mast cells progenitor cells, monocytes,
some granulocytes and endothelial cells. Table 1 shows the
summary of MDSC (CD11b+Gr1+) frequencies before and
after isolation from naïve and tumor-bearing mice. In addi-
tion, it shows the calculated percentage of target cells
recovered after isolation.

Example 19: Isolation of MDSCs from Spleens
Harvested from Tumour-Bearing Mice Using the
Sixth Antibody Cocktail in a Direct Approach are
Functional Since MDSCs are defined functionally and not necessarily
phenotypically, isolated cells were assayed for their ability to suppress the activation of other immune cells. To do this
a T cell suppression assay was conducted as follows: sple-
nocytes from naïve mice were labeled with cell proliferation
dye and the T cells (within the whole splenocytes) were
stimulated, or not, with anti-CD3 and anti-CD28 (polyclonal
stimulation) to induce proliferation. MDSCs isolated from
B16 tumour-bearing C57BI/6 mice were added to the stimu-
lated splenocytes at different ratios. Proliferation and IFNg
production was determined after 4 days. As can be seen in
FIG. 13A there is a dose dependent effect of MDSCs on the
proliferation of both CD4 and CD8 T cells. In addition,
suppression of IFNg was also MDSC dose dependent (FIG.
13B). This confirmed that the isolated cells are functional.

TABLE 1

| | Naïve Start | Naïve Isolated | Tumour Start | Tumour Isolated |
|---|---|---|---|---|
| Average % Purity (mean ± SD) | 4.2 ± 1.2 | 86 ± 4.6 | 33.5 ± 21.6 | 94.3 ± 2.1 |
| Average % Recovery (mean ± SD | | 53.8 ± 22.1 | | 50.1 ± 12.3 |
| n | 14 | 14 | 9 | 9 |

The invention claimed is:

1. A kit for one-step enrichment of myeloid-derived
suppressor cells (MDSCs) from a sample comprising target
cells and MDSCs, the kit comprising:

a plurality of antibodies or fragments thereof that bind
target cells;

a blocking agent that blocks unintended binding of the
antibodies or fragments thereof by Fc receptors
expressed on the target cells; and a plurality of particles, wherein the plurality of particles
are linked or linkable to at least one of the antibodies
or fragments thereof, wherein the kit recovers at least 40% of the MDSCs in the
sample at a purity of about 70% or higher of the
MDSCs, as assessed by flow cytometry, wherein the target cells comprise B cells, T cells, NK
cells, dendritic cells, mast cells, granulocytes, red blood
cells, and hematopoietic progenitors, and wherein the plurality of antibodies comprise a) an anti-CD8 antibody, an anti-B220 antibody, an anti-
Ter-119 antibody, an anti-CD49b antibody, an anti-
CD19 antibody, an anti-CD11c antibody, an anti-
TCRγ/δ antibody, an anti-CD24 antibody, an anti-
TCRα/β antibody, an anti-CD4 antibody, an anti-CD5
antibody, an anti-CD2 antibody, an anti-cKit antibody,
and an anti-F480 antibody, b) an anti-CD8 antibody, an anti-B220 antibody, an anti-
Ter-119 antibody, an anti-CD49b antibody, an anti-
CD19 antibody, an anti-CD11c antibody, an anti-
TCRγ/δ antibody, an anti-CD24 antibody, an anti-
TCRα/β antibody, an anti-CD4 antibody, an anti-CD5
antibody, an anti-CD2 antibody, and an anti-cKit anti-
body, c) an anti-CD8 antibody, an anti-B220 antibody, an anti-
Ter-119 antibody, an anti-CD49b antibody, an anti-
CD19 antibody, an anti-CD11c antibody, an anti-
TCRγ/δ antibody, an anti-CD24 antibody, an anti-
TCRα/β antibody, an anti-CD4 antibody, an anti-CD5
antibody, an anti-CD2 antibody, an anti-cKit antibody,
and an anti-CD31 antibody, d) an anti-CD8 antibody, an anti-Ter-119 antibody, an
anti-CD49b antibody, an anti-CD19 antibody, an anti- CD11c antibody, an anti-TCRγ/δ antibody, an anti-CD24 antibody, an anti-TCRα/β antibody, an anti-CD4 antibody, an anti-CD5 antibody, an anti-CD2 antibody, an anti-cKit antibody, and an anti-CD31 antibody, or e) an anti-CD8 antibody, an anti-B220 antibody, an anti-Ter-119 antibody, an anti-CD49b antibody, an anti-CD19 antibody, an anti-CD11c antibody, an anti-TCRγ/δ antibody, an anti-TCRα/β antibody, an anti-CD4 antibody, an anti-CD5 antibody, an anti-CD2 antibody, an anti-cKit antibody, and an anti-CD31 antibody.

2. A kit for one-step enrichment of myeloid-derived suppressor cells (MDSCs) from a sample comprising target cells and MDSCs, the kit comprising:

a plurality of antibodies or fragments thereof that bind target cells;

a blocking agent that blocks unintended binding of the antibodies or fragments thereof by Fc receptors expressed on the target cells; and a plurality of particles, wherein the plurality of particles are linked or linkable to at least one of the antibodies or fragments thereof, wherein the kit recovers at least 40% of the MDSCs in the sample at a purity of about 70% or higher of the MDSCs, as assessed by flow cytometry, wherein the target cells comprise B cells, T cells, NK cells, dendritic cells, monocytes/macrophages, mast cells, endothelial cells, granulocytes, red blood cells, and hematopoietic progenitors, and wherein the plurality of antibodies comprise a) an anti-CD8 antibody, an anti-B220 antibody, an anti-Ter-119 antibody, an anti-CD49b antibody, an anti-CD19 antibody, an anti-CD11c antibody, an anti-TCRγ/δ antibody, an anti-CD24 antibody, an anti-TCRα/β antibody, an anti-CD4 antibody, an anti-CD5 antibody, an anti-CD2 antibody, an anti-cKit antibody, and an anti-F480 antibody, b) an anti-CD8 antibody, an anti-B220 antibody, an anti-Ter-119 antibody, an anti-CD49b antibody, an anti-CD19 antibody, an anti-CD11c antibody, an anti-TCRγ/δ antibody, an anti-CD24 antibody, an anti-TCRα/β antibody, an anti-CD4 antibody, an anti-CD5 antibody, an anti-CD2 antibody, and an anti-cKit antibody, c) an anti-CD8 antibody, an anti-B220 antibody, an anti-Ter-119 antibody, an anti-CD49b antibody, an anti-CD19 antibody, an anti-CD11c antibody, an anti-TCRγ/δ antibody, an anti-CD24 antibody, an anti-TCRα/β antibody, an anti-CD4 antibody, an anti-CD5 antibody, an anti-CD2 antibody, an anti-cKit antibody, and an anti-CD31 antibody, d) an anti-CD8 antibody, an anti-Ter-119 antibody, an anti-CD49b antibody, an anti-CD19 antibody, an anti-CD11c antibody, an anti-TCRγ/δ antibody, an anti-CD24 antibody, an anti-TCRα/β antibody, an anti-CD4 antibody, an anti-CD5 antibody, an anti-CD2 antibody, an anti-cKit antibody, and an anti-CD31 antibody, or e) an anti-CD8 antibody, an anti-B220 antibody, an anti-Ter-119 antibody, an anti-CD49b antibody, an anti-CD19 antibody, an anti-CD11c antibody, an anti-TCRγ/δ antibody, an anti-TCRα/β antibody, an anti-CD4 antibody, an anti-CD5 antibody, an anti-CD2 antibody, an anti-cKit antibody, and an anti-CD31 antibody.

3. The kit according to claim 1, wherein the plurality of antibodies or fragments thereof bind one or more antigens or epitopes thereof on the target cells, and wherein:

i) the B cell antigens are selected from B220, CD19, CD2, CD5, and CD31;

ii) the T cell antigens are selected from CD8, TCRγ/δ, TCRα/β, CD4, CD5, CD2, and CD31;

iii) the NK cell antigens are selected from CD49b and CD2;

iv) the dendritic cell antigens are selected from CD11c and CD31;

v) the mast cell antigen is cKit;

vi) the granulocyte antigen is CD31; and vii) the red blood cell antigens are selected from Ter119 and CD24.

4. The kit according to claim 1, wherein the plurality of antibodies comprise a first linkage moiety.

5. The kit according to claim 4, wherein the plurality of particles comprise a second linkage moiety directly or indirectly linked or linkable to the first linkage moiety.

6. The kit according to claim 5, wherein the first linkage moiety is biotin, or any modification, derivative, or analogue thereof, and the second linkage moiety is streptavidin, or any modification, derivative, or analogue thereof.

7. The kit according to claim 5, wherein the kit further comprises a tetrameric antibody complex (TAC), wherein the TAC comprises a first antibody that binds to the first linkage moiety and a second antibody that binds to the second linkage moiety and the first antibody and the second antibody are indirectly linked.

8. The kit according to claim 1, wherein the plurality of particles are magnetic or magnetizable.

9. A method for one-step enrichment of myeloid-derived suppressor cells (MDSCs) from a sample comprising target cells and MDSCs, the method comprising:

blocking unintended binding of a plurality of antibodies or fragments thereof by Fc receptors on the one or more target cells with a blocking agent;

contacting the sample with the plurality of antibodies or fragments thereof that bind one or more target cells, and a plurality of particles, wherein the plurality of particles are linked or linkable to at least one of the antibodies or fragments thereof;

incubating the target cells, antibodies or fragments thereof, and particles to form target cell:particle complexes; and separating the target cell:particle complexes from the sample to enrich the MDSCs, wherein the kit recovers at least 40% of the MDSCs in the sample at a purity of about 70% or higher of the MDSCs, as assessed by flow cytometry, wherein the target cells comprise B cells, T cells, NK cells, dendritic cells, mast cells, granulocytes, red blood cells, and hematopoietic progenitors, and wherein the plurality of antibodies comprise a) an anti-CD8 antibody, an anti-B220 antibody, an anti-Ter-119 antibody, an anti-CD49b antibody, an anti-CD19 antibody, an anti-CD11c antibody, an anti-TCRγ/δ antibody, an anti-CD24 antibody, an anti-TCRα/β antibody, an anti-CD4 antibody, an anti-CD5 antibody, an anti-CD2 antibody, an anti-cKit antibody, and an anti-F480 antibody, b) an anti-CD8 antibody, an anti-B220 antibody, an anti-Ter-119 antibody, an anti-CD49b antibody, an anti-CD19 antibody, an anti-CD11c antibody, an anti-TCRγ/δ antibody, an anti-CD24 antibody, an anti-TCRα/β antibody, an anti-CD4 antibody, an anti-CD5 antibody, an anti-CD2 antibody, and an anti-cKit antibody, c) an anti-CD8 antibody, an anti-B220 antibody, an anti-Ter-119 antibody, an anti-CD49b antibody, an anti-CD19 antibody, an anti-CD11c antibody, an anti-TCRγ/δ antibody, an anti-CD24 antibody, an anti-TCRα/β antibody, an anti-CD4 antibody, an anti-CD5 antibody, an anti-CD2 antibody, an anti-cKit antibody, and an anti-CD31 antibody, d) an anti-CD8 antibody, an anti-Ter-119 antibody, an anti-CD49b antibody, an anti-CD19 antibody, an anti-CD11c antibody, an anti-TCRγ/δ antibody, an anti-CD24 antibody, an anti-TCRα/β antibody, an anti-CD4 antibody, an anti-CD5 antibody, an anti-CD2 antibody, an anti-cKit antibody, and an anti-CD31 antibody, or e) an anti-CD8 antibody, an anti-B220 antibody, an anti-Ter-119 antibody, an anti-CD49b antibody, an anti-CD19 antibody, an anti-CD11c antibody, an anti-TCRγ/δ antibody, an anti-TCRα/β antibody, an anti-CD4 antibody, an anti-CD5 antibody, an anti-CD2 antibody, an anti-cKit antibody, and an anti-CD31 antibody.

10. The method according to claim 9, wherein the target cells further comprise one or more of monocytes/macrophages, basophils, platelets, and endothelial cells.

11. The method according to claim 10, wherein the plurality of antibodies or fragments thereof bind one or more antigens or epitopes thereof on the target cells, and wherein:

i) the B cell antigens are selected from B220, CD19, CD2, CD5, and CD31:

ii) the T cell antigens are selected from CD8, TCRγ/δ, TCRα/β, CD4, CD5, CD2, and CD31;

iii) the NK cell antigens are selected from CD49b and CD2;

iv) the dendritic cell antigens are selected from CD11c and CD31:

v) the mast cell antigen is cKit;

vi) the granulocyte antigen is CD31; and vii) the red blood cell antigens are selected from Ter119 and CD24.

12. The method according to claim 9, wherein the plurality of antibodies comprise a first linkage moiety.

13. The method according to claim 12, wherein the plurality of particles comprise a second linkage moiety directly or indirectly linked or linkable to the first linkage moiety.

14. The method according to claim 13, wherein the first linkage moiety is biotin, or any modification, derivative, or analogue thereof, and the second linkage moiety is streptavidin, or any modification, derivative, or analogue thereof.

15. The method according to claim 9, further comprising pre-linking the antibodies and particles before contacting the sample.

16. The method according to claim 9, wherein the plurality of particles are magnetic or magnetizable.

17. The method according to claim 16, further comprising exposing the target cell:particle complexes to a magnetic field.

18. The method according to claim 9, wherein the sample is a cell suspension.

19. The method according to claim 18, wherein the cell suspension is obtained from a tumour, spleen tissue, bone marrow tissue, or blood.

20. The kit of claim 1, wherein the target cells further comprise monocytes/macrophages and endothelial cells, and optionally one or more of basophils, and platelets.

*   *   *   *   *